US007320680B2

(12) United States Patent
Shue et al.

(10) Patent No.: US 7,320,680 B2
(45) Date of Patent: Jan. 22, 2008

(54) SINGLE-USE SYRINGE

(76) Inventors: Ming-Jeng Shue, No. 14, Lane 8, Chung-I St., Hsi Dist., Taichung City (TW); Deborah Huang, 7F, No. 5, Sec. 3, Liu-Chun E. St., Chung Dist., Taichung City (TW); Phillip Shue, No. 14, Lane 8, Chung-I St., Hsi Dist., Taichung City (TW)

( * ) Notice: Subject to any disclaimer, the term of this patent is extended or adjusted under 35 U.S.C. 154(b) by 149 days.

(21) Appl. No.: 10/928,030

(22) Filed: Aug. 26, 2004

(65) Prior Publication Data

US 2005/0261627 A1    Nov. 24, 2005

(30) Foreign Application Priority Data

May 21, 2004   (TW) ................................ 93114444 A

(51) Int. Cl.
*A61M 5/00* (2006.01)
(52) U.S. Cl. ...................... 604/110; 604/222; 604/228; 604/229
(58) Field of Classification Search ................ 604/110, 604/218, 228, 229, 111, 222, 181, 187; 128/919
See application file for complete search history.

(56) References Cited

U.S. PATENT DOCUMENTS 5,000,735 A * 3/1991 Whelan ...................... 604/110
5,201,709 A * 4/1993 Capra et al. ................ 604/110

* cited by examiner

*Primary Examiner*—Kevin C. Sirmons
*Assistant Examiner*—Laura C. Schell
(74) *Attorney, Agent, or Firm*—Townsend and Townsend and Crew LLP

(57) ABSTRACT

A single-use syringe includes a barrel having front and rear passageways and a shoulder disposed there between, a plunger movable in the rear passageway, a carrier having a tail portion extending from a front end wall of the plunger, and pushing and retained regions formed forwardly of the tail portion, and a deformable sealing member in fluid-tight and slidable engagement with the barrel. The sealing member includes an inner surrounding wall surface with a yielding segment engaging the pushing region, and a retaining segment in frictional engagement with the retained region by a frictional force so as to confine a fluid-tight surrounding area. The frictional force is diminished when the yielding segment is depressed by the pushing region so as to facilitate release of the retained region from the retaining segment, thereby disrupting the fluid-tightness of the surrounding area and rendering the syringe unreusable.

14 Claims, 25 Drawing Sheets

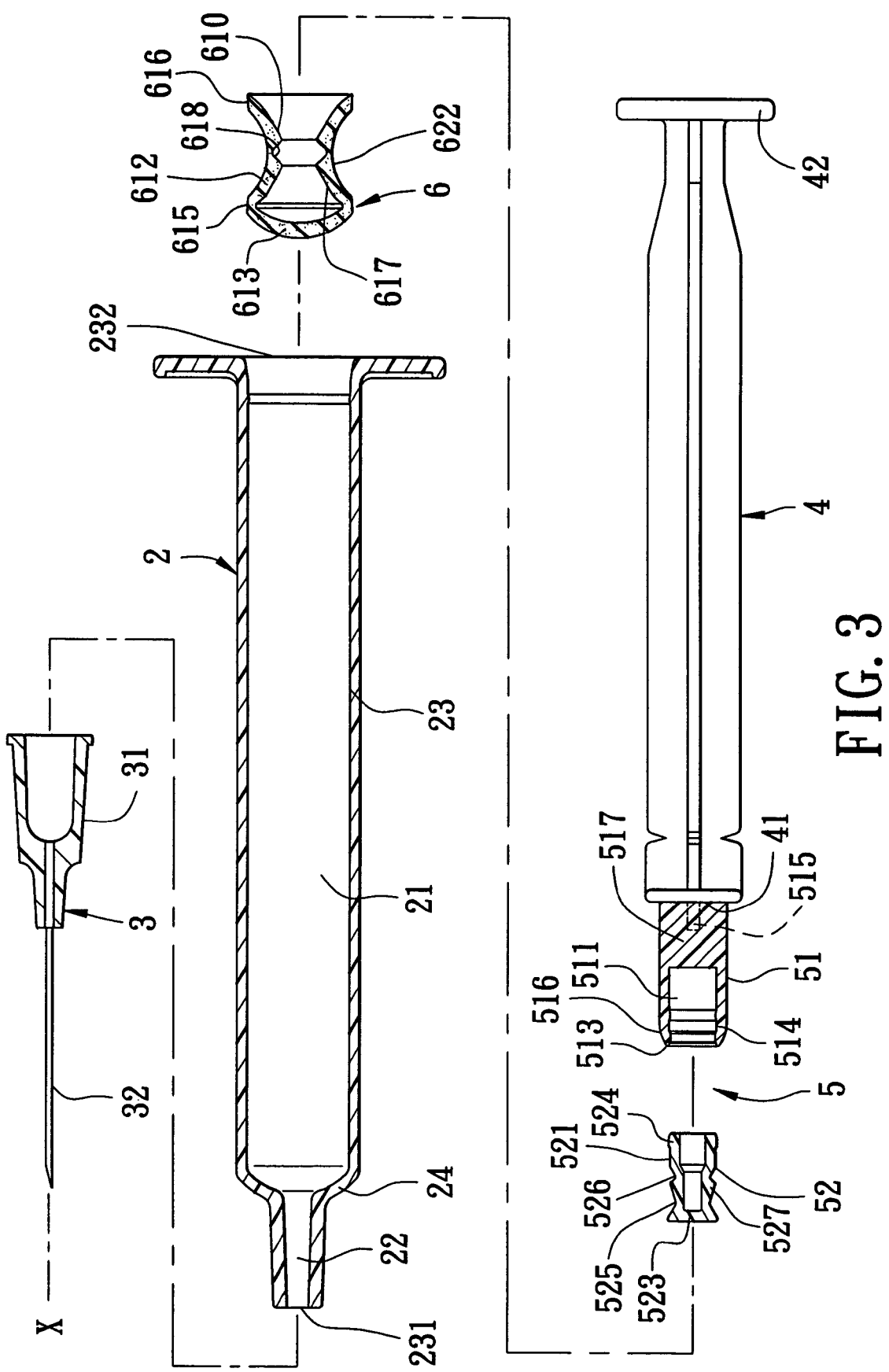

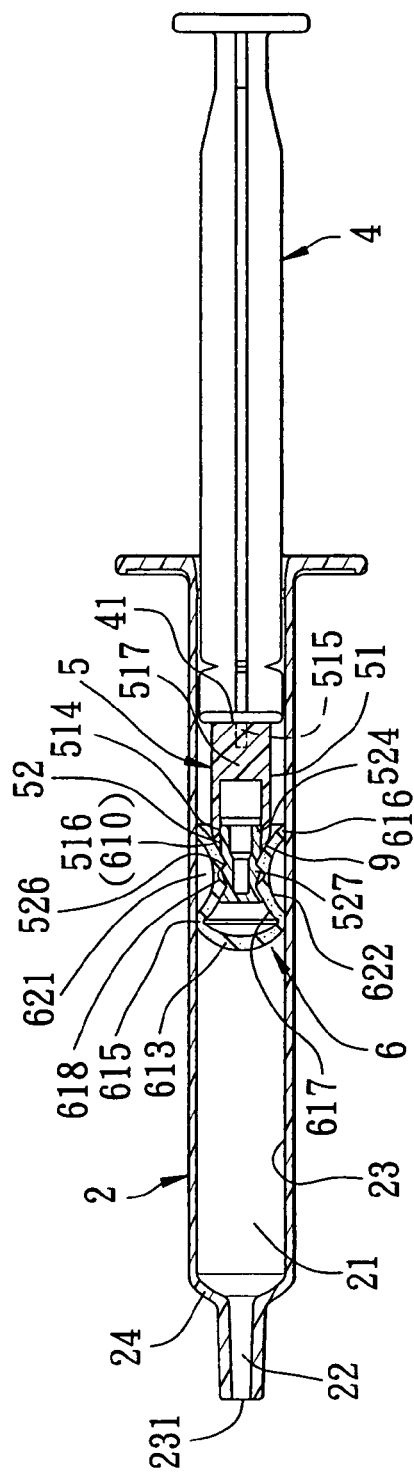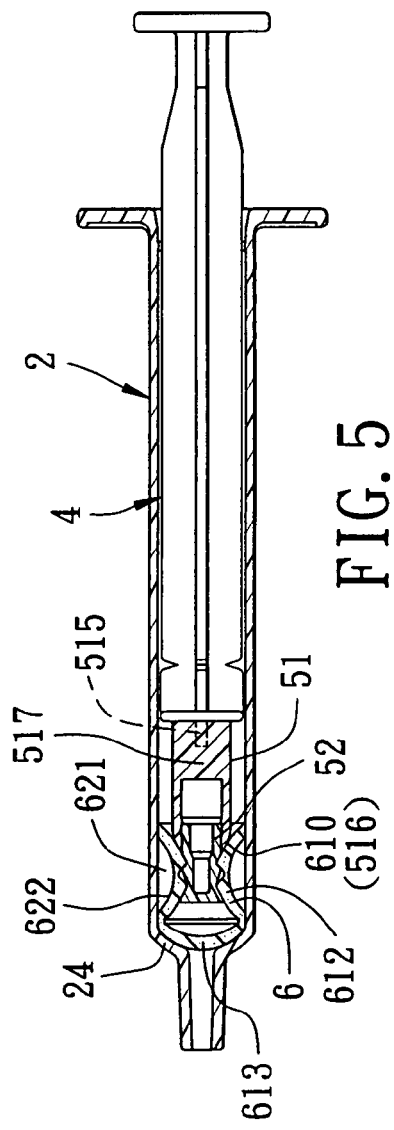

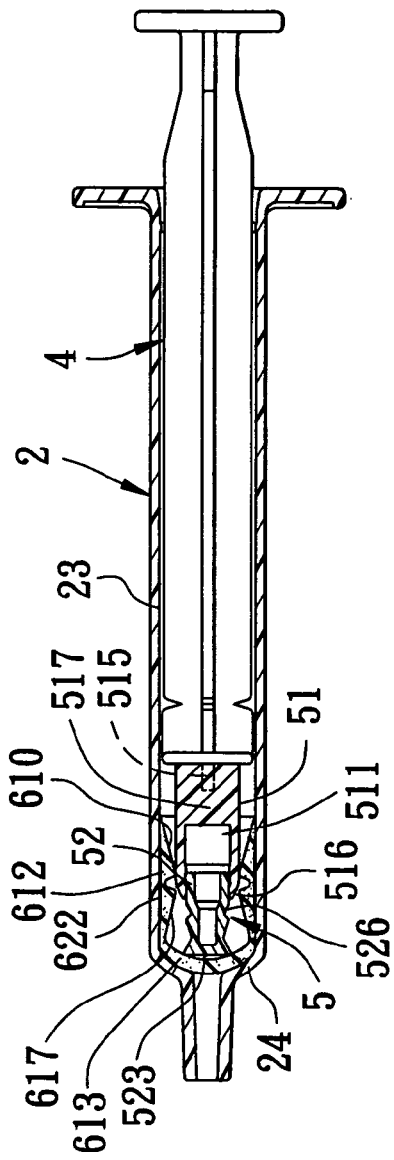
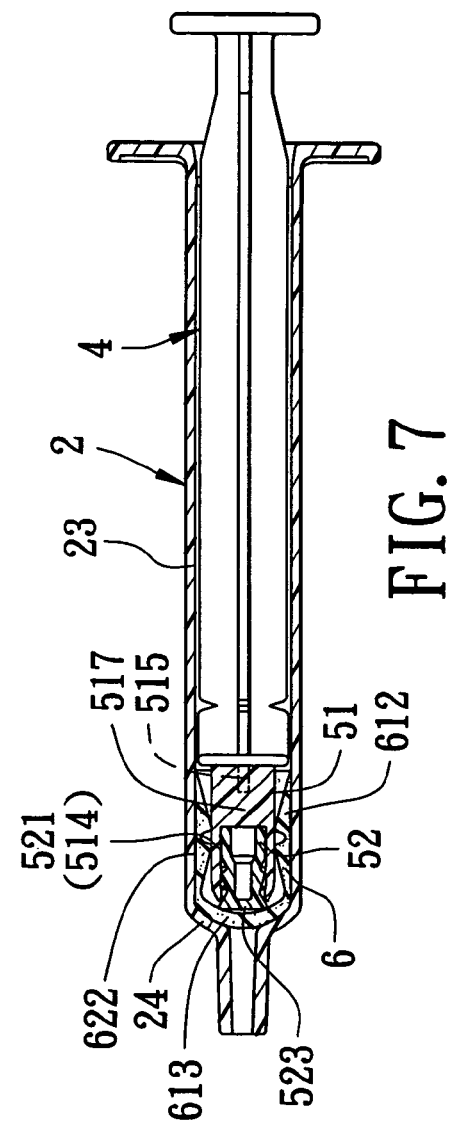
FIG. 6
FIG. 7

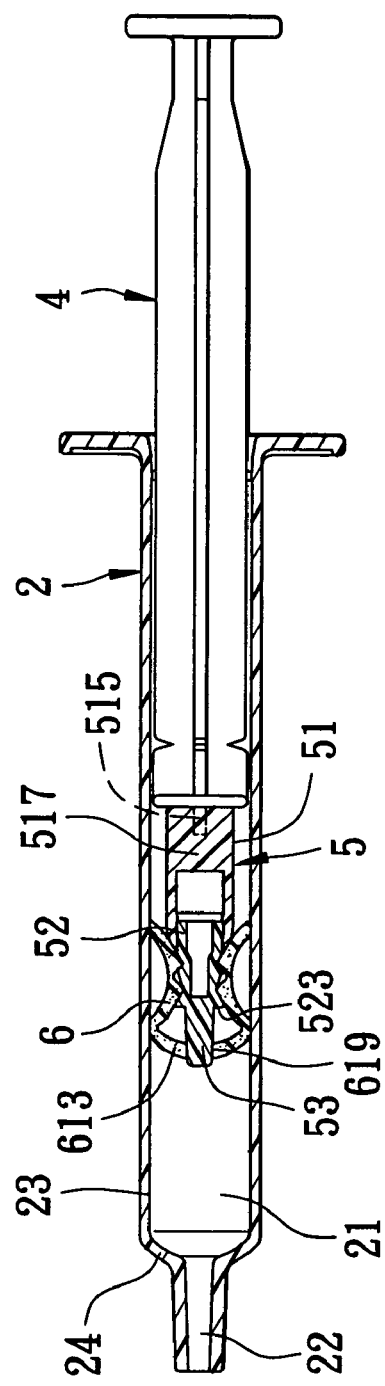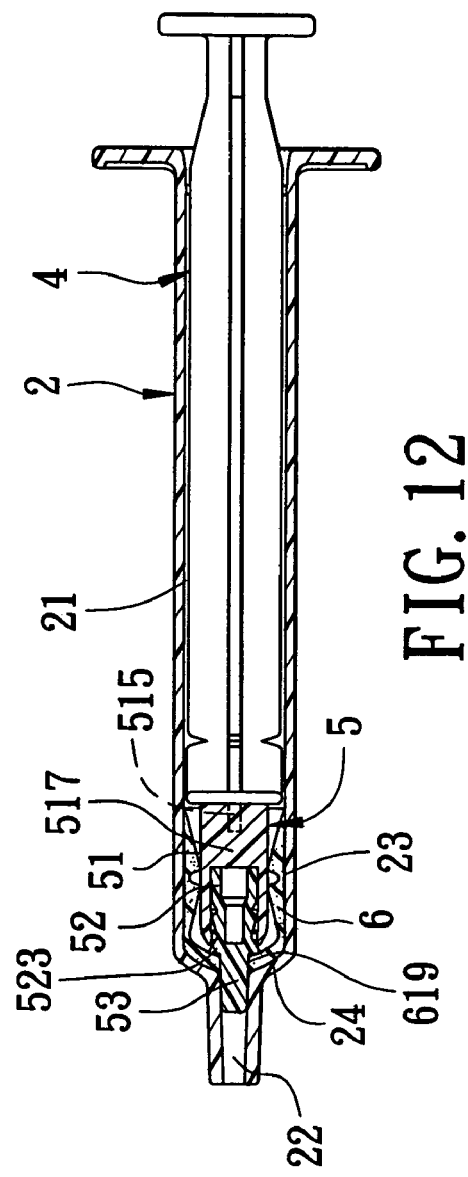
FIG. 11
FIG. 12

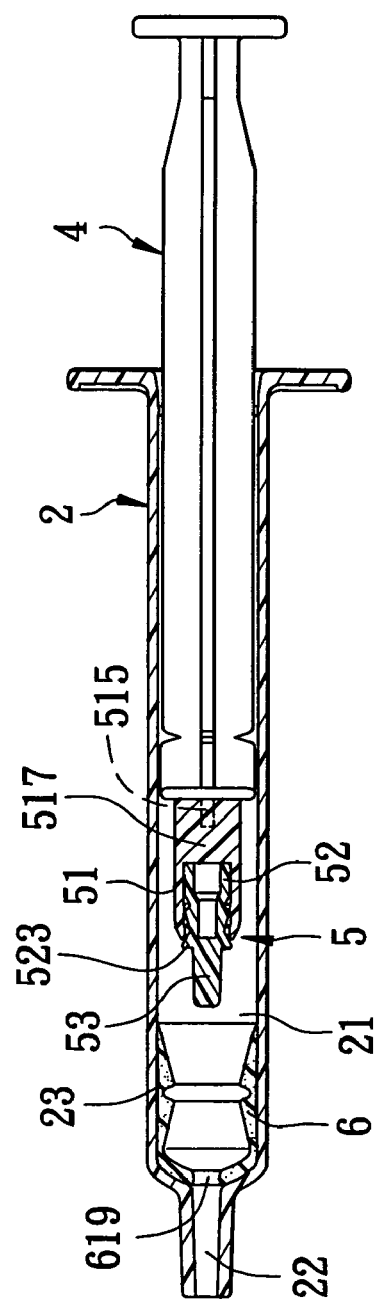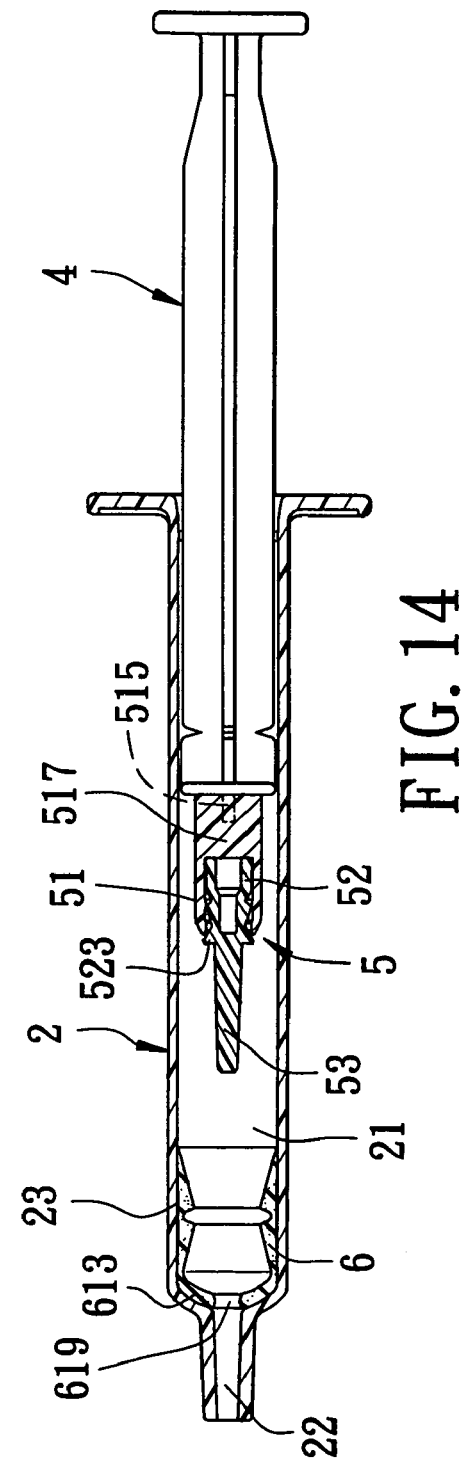

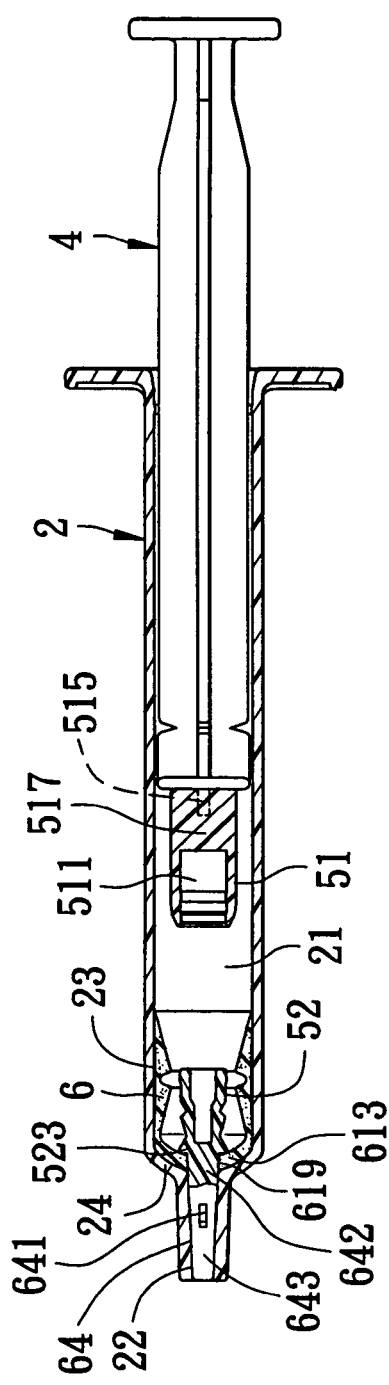
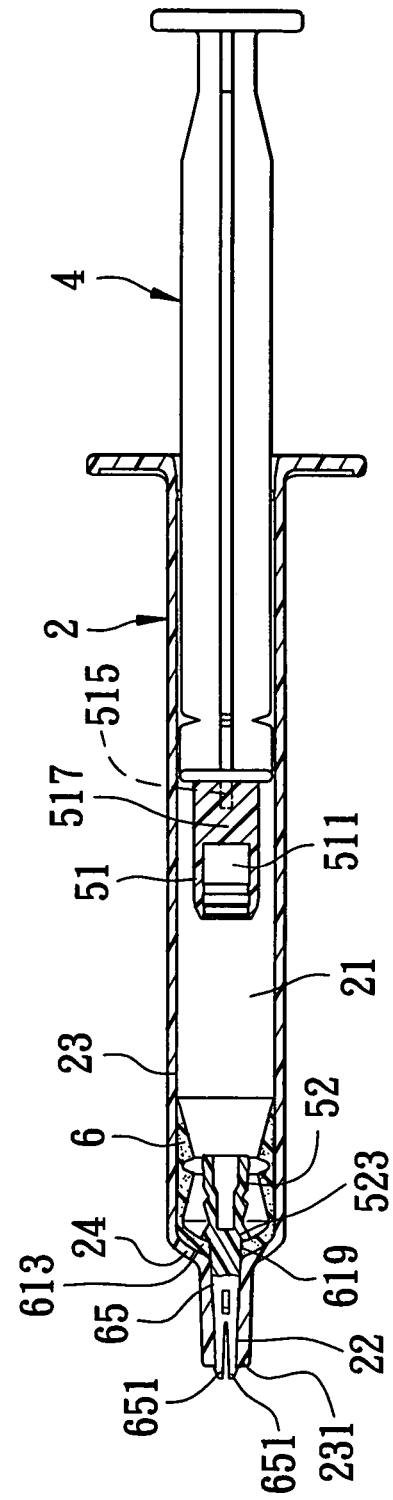

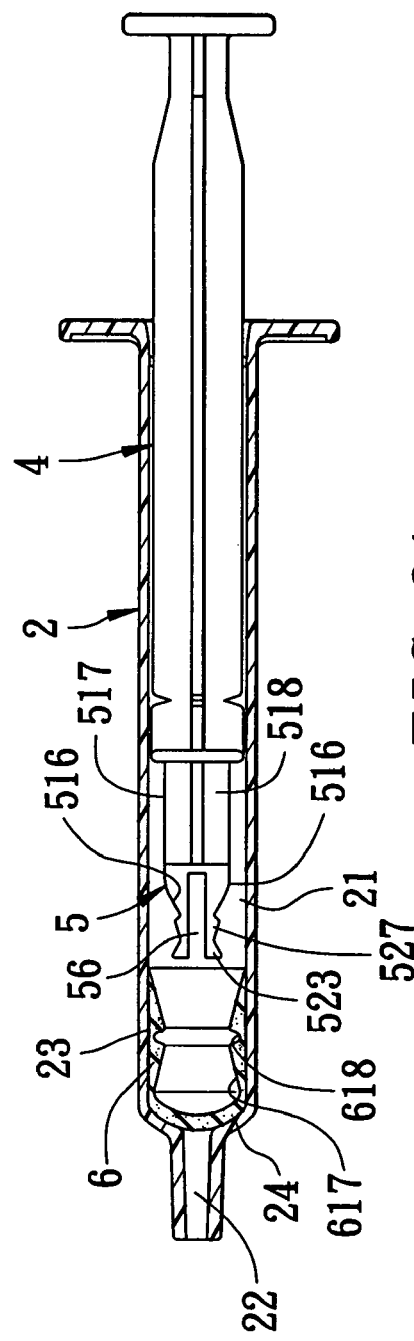
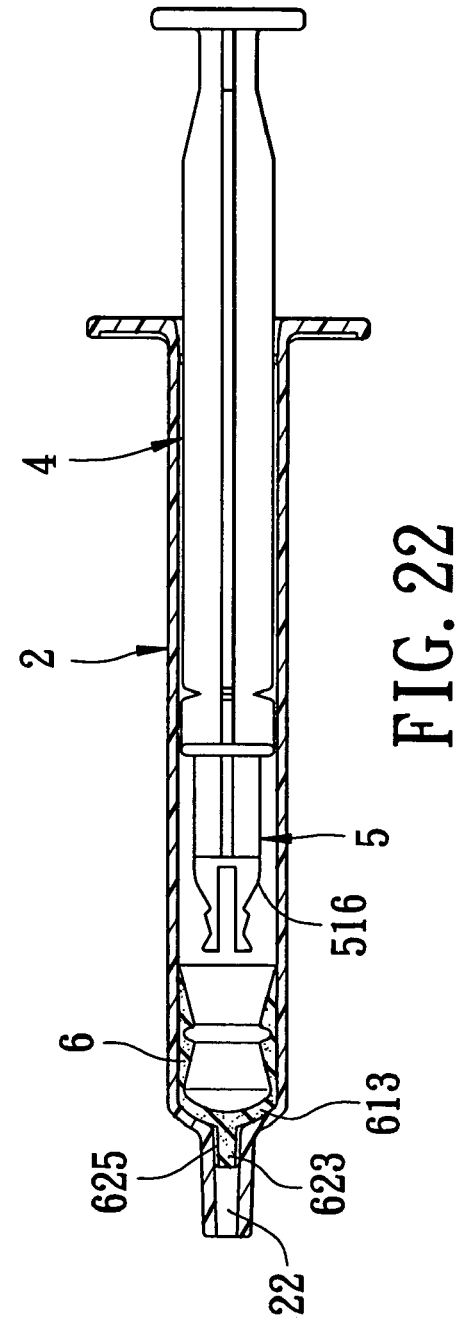

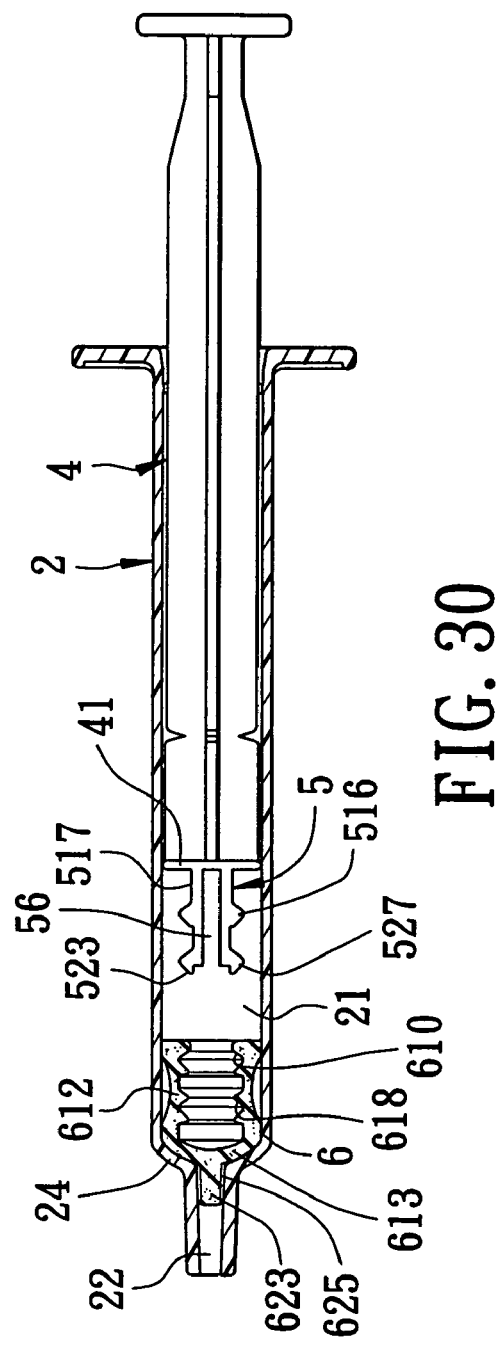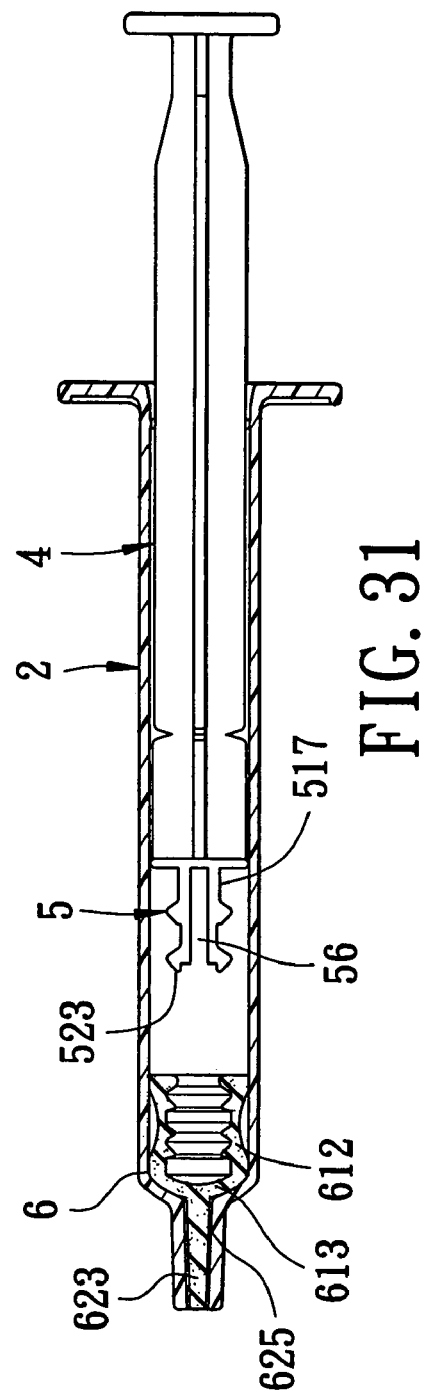

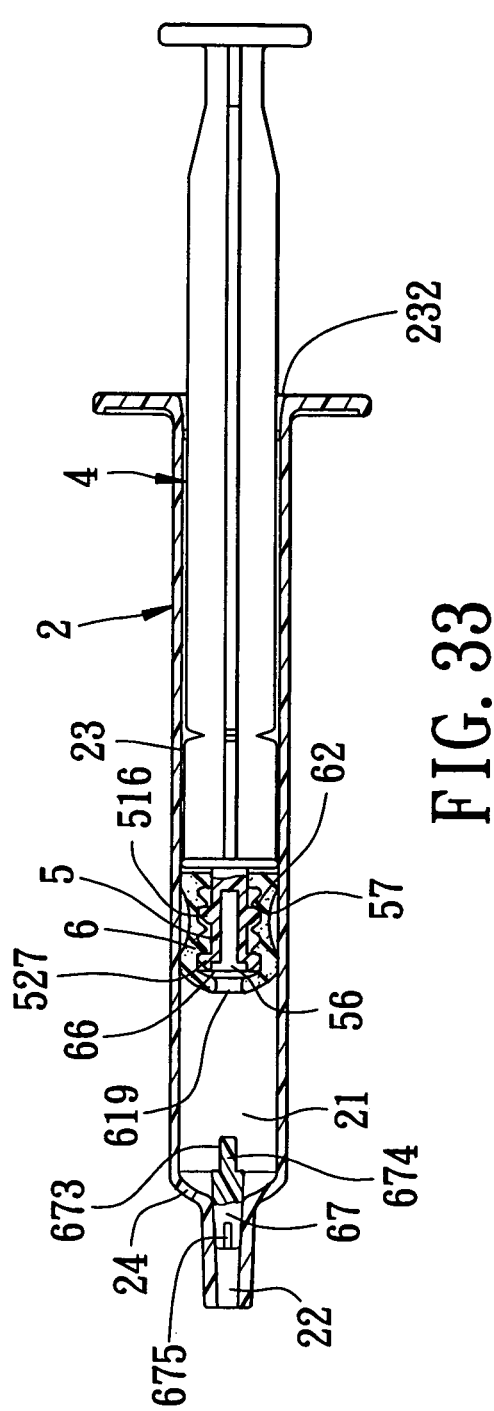
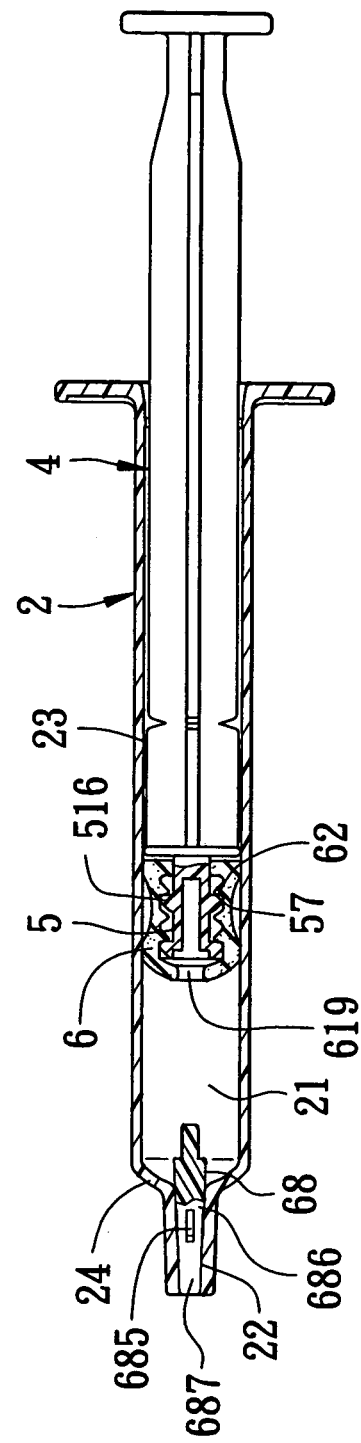
FIG. 33
FIG. 34

SINGLE-USE SYRINGE

BACKGROUND OF THE INVENTION

1. Field of the Invention

This invention relates to a single-use syringe, more particularly to a single-use syringe in which fluid-tightness of a barrel is disrupted when the syringe is displaced to a disposal position so as to render the syringe unreusable.

2. Description of the Related Art

Referring to FIGS. 1 and 2, a conventional single-use syringe is shown to include a barrel 11 which has an axially extending surrounding wall 113 defining front and rear passageways 112, 111, and a surrounding shoulder 114 disposed between the front and rear passageways 112, 111, a needle assembly 12 which is sleeved on a front opened end of the surrounding wall 113, a plunger 13 which is disposed to be movable in and along the rear passageway 111 and which has a tapered head 131 formed on a front end thereof, a deformable sealing member 14 which is retainingly sleeved on the tapered head 131, which is in fluid-tight and slidable engagement with the surrounding wall 113 at the rear passageway 111, and which has an axially extending vent hole 132 communicated with the ambient air, and a plug 15 which is detachably connected to the deformable sealing member 14 and which closes the vent hole 132. An inner surface of the surrounding wall 113 has a retaining ring 115 formed adjacent to the shoulder 114. The plug 15 has an anchoring portion 151 projecting forwardly and outwardly of the deformable sealing member 14 such that, subsequent to completion of injection, the deformable sealing member 14 is brought to abut against the shoulder 114 and the anchoring portion 151 is engaged with the retaining ring 115 to thereby permit disengagement of the plug 15 from the deformable sealing member 14 when the plunger 13 is pulled rearwardly, and to thereby disrupt the fluid-tightness of the vent hole 132 for rendering the syringe unreusable. However, when the anchoring portion 151 is forced to be engaged with the retaining ring 115, the frictional force between the plug 15 and the deformable sealing member 14 is increased, which may be greater than the force of engagement between the anchoring portion 151 and the retaining ring 115, thereby adversely affecting separation of the plug 15 from the deformable sealing member 14. Moreover, formation of the retaining ring 115 on the inner surface of the barrel 11 is inconvenient during manufacture.

SUMMARY OF THE INVENTION

An object of the present invention is to provide a single-use syringe which has friction diminishing means to facilitate disruption of fluid-tightness of a surrounding area in a barrel when the syringe is displaced to a disposal position so as to render the syringe unreusable.

According to this invention, the single-use syringe includes a barrel having an inner surrounding barrel surface which surrounds an axis in a longitudinal direction, and which includes a rear larger-diameter portion that defines a rear passageway therein, a front smaller-diameter portion that defines a front passageway therein to be in fluid communication with a needle assembly and that is opposite to the rear larger-diameter portion in the longitudinal direction, and a surrounding shoulder that is disposed between the rear larger-diameter portion and the front smaller-diameter portion. The rear passageway terminates at a rearward opening.

A plunger is disposed to be movable in the rear passageway along the larger-diameter portion. The plunger has a front end wall which confronts the front passageway, and a rear end wall which is disposed opposite to the front end wall and which extends outwardly of the rearward opening to be manually operable.

A carrier includes a tail portion which extends from the front end wall along the axis, a head portion which is disposed opposite to the tail portion in the rear passageway along the axis, and an intermediate surrounding portion which is interposed between the tail and head portions and which surrounds the axis. The intermediate surrounding portion has a pushing region and a retained region which are proximate to the tail and head portions, respectively.

A hollow deformable sealing member includes a head end wall which has a periphery and which confronts the surrounding shoulder, an upper sealing end which is integrally formed with the periphery of the head end wall and which is in fluid-tight and slidable engagement with the rear larger-diameter portion, and a deformable surrounding wall which extends from the upper sealing end rearwardly and which terminates at a surrounding trailing end that is configured to drag on the rear larger-diameter portion. The deformable surrounding wall has an outer surrounding wall surface which is spaced apart from the rear larger-diameter portion in radial directions when the syringe is in a position of use, thereby vesting the deformable surrounding wall with an increased radial flexibility, and an inner surrounding wall surface which is opposite to the outer surrounding wall surface in radial directions. The inner surrounding wall surface has a yielding segment which is engaged with and which is depressed by the pushing region radially when the carrier is moved in a longitudinal direction relative to the deformable surrounding wall so as to bring the head end wall to abut against and to be retained at the surrounding shoulder, thereby displacing the syringe from the position of use to a disposal position, and a retaining segment which is in a frictional engagement with the retained region by virtue of a frictional force so as to confine, in cooperation with the yielding segment and the pushing region, a fluid-tight surrounding area, and which is configured such that the frictional force is diminished so as to facilitate release of the retained region from the retaining segment when the yielding segment is depressed by the pushing region, thereby disrupting the fluid-tightness of the surrounding area and rendering the syringe unreusable.

BRIEF DESCRIPTION OF THE DRAWINGS

Other features and advantages of the present invention will become apparent in the following detailed description of the preferred embodiments of the invention, with reference to the accompanying drawings, in which:

FIG. 3 is an exploded sectional view of the first preferred embodiment of a single-use syringe according to this invention;

FIG. 4 is a sectional view of the first preferred embodiment during an injection stroke;

FIG. 5 is a sectional view of the first preferred embodiment, showing the state of completion of the injection stroke;

FIGS. 6 to 8 are sectional views of the first preferred embodiment, showing an operation of disrupting fluid-tightness of the syringe;

FIG. 11 is a sectional view of the third preferred embodiment of a single-use syringe according to this invention;

FIGS. 12 and 13 are sectional views of the third preferred embodiment, showing an operation of disrupting fluid-tightness of the syringe;

FIG. 14 is a sectional view of a modified form of the third preferred embodiment shown in FIG. 11;

FIG. 17 is a sectional view of a modified form of the fourth preferred embodiment shown in FIG. 15;

FIG. 18 is a sectional view of another modified form of the fourth preferred embodiment shown in FIG. 15;

FIGS. 20 and 21 are sectional views of the fifth preferred embodiment, showing an operation of disrupting fluid-tightness of the syringe;

FIG. 22 is a sectional view of the sixth preferred embodiment of a single-use syringe according to this invention;

FIG. 30 is a sectional view of the tenth preferred embodiment after disruption of the fluid-tightness of the syringe;

FIG. 31 is a sectional view of a modified form of the tenth preferred embodiment shown in FIG. 29;

FIG. 33 is a sectional view of the eleventh preferred embodiment after disruption of the fluid-tightness of the syringe;

FIG. 34 is a sectional view of a modified form of the eleventh preferred embodiment shown in FIG. 32;

DETAILED DESCRIPTION OF THE PREFERRED EMBODIMENTS

Figure 1:
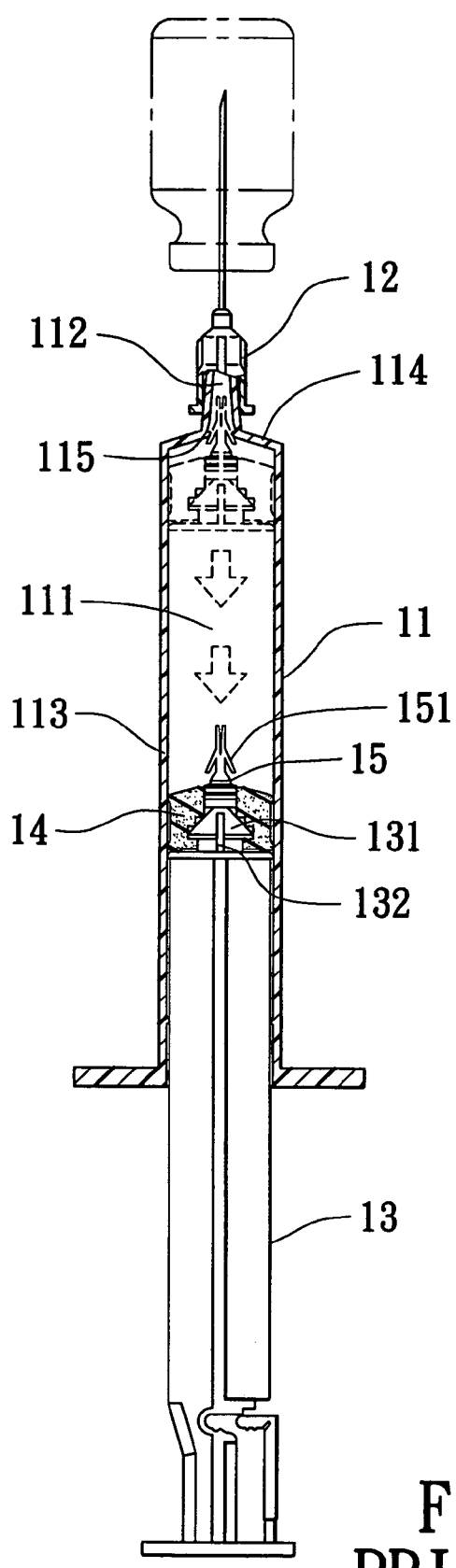
FIG. 1 is a sectional view of a conventional single-use syringe.
Figure 2:
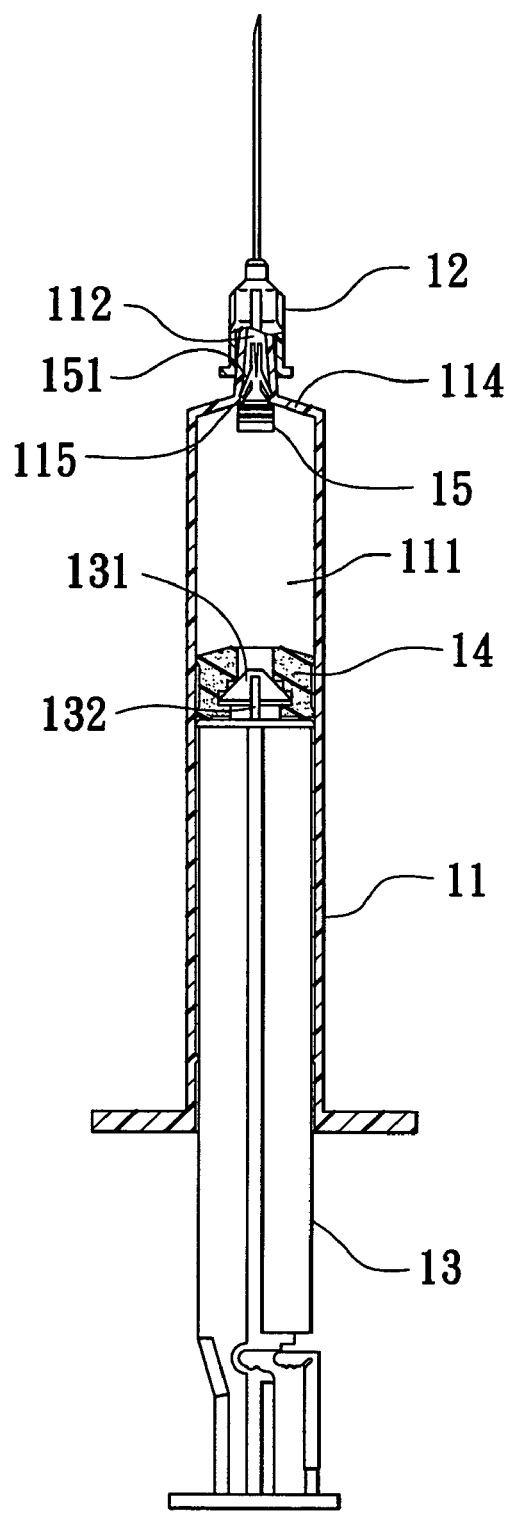
FIG. 2 is a sectional view of the conventional single-use syringe of FIG. 1 after use.

Before the present invention is described in greater detail, it should be noted that same reference numerals have been used to denote like elements throughout the specification.

Referring to FIGS. 3 and 4, the first preferred embodiment of a single-use syringe according to the present invention is shown to be used with a needle assembly 3. The needle assembly 3 includes a needle hub 31 and a needle cannula 32. The syringe comprises a barrel 2, a plunger 4, a carrier 5, and a hollow deformable sealing member 6.

The barrel 2 has an inner surrounding barrel surface 23 which surrounds an axis (X) in a longitudinal direction, and which includes a rear larger-diameter portion that defines a rear passageway 21 therein, a front smaller-diameter portion that defines a front passageway 22 therein to be in fluid communication with the needle assembly 3 in a known manner, and that is opposite to the rear larger-diameter portion in the longitudinal direction, and a surrounding shoulder 24 that is disposed between the rear larger-diameter portion and the front smaller-diameter portion. The front and rear passageways 22,21 respectively terminate at forward and rearward openings 231,232.

The plunger 4 is disposed to be movable in the rear passageway 21 along the larger-diameter portion. The plunger 4 has a front end wall 41 which confronts the front passageway 22, and a rear end wall 42 which is disposed opposite to the front end wall 41 along the longitudinal direction and which extends outwardly of the rearward opening 232 to be manually operable.

The carrier 5 includes a tail portion 517 which extends from the front end wall 41 along the axis (X), a head portion 523 which is disposed in the rear passageway 21 opposite to the tail portion 517 and along the axis (X), and an intermediate surrounding portion which is interposed between the tail and head portions 517,523 and which surrounds the axis (X). The intermediate surrounding portion includes a tubular pushing segment 51 and a tubular retained segment 52. The pushing segment 51 is coupled and formed integrally with the tail portion 517, and terminates at an opened end 513. The pushing segment 51 has an inner surrounding engaging region 514 which extends in the longitudinal direction to be communicated with the opened end 513 and which defines a cavity 511, and a pushing region 516 which is disposed radially and outwardly of the inner surrounding engaging region 514. Preferably, the pushing segment 51 is converged from the pushing region 516 to the opened end 513. A vent hole 515 is formed in the pushing segment 51, and extends along the axis (X) to be in fluid communication with the cavity 511. The retained segment 52 has an outer surrounding retained wall 521 which extends from the head portion 523 in the longitudinal direction to terminate at an outer engaging end 524 and which is insertable into the cavity 511. The outer surrounding retained wall 521 has two annular grooves 525,526, and a projecting retained region 527 formed between the annular grooves 525,526. In a position of use, as shown in FIG. 4, the outer engaging end 524 is frictionally engaged with the inner surrounding engaging region 514 such that the annular grooves 525,526 and the retained region 527 are projected outwardly of the pushing segment 51.

Figure 8:
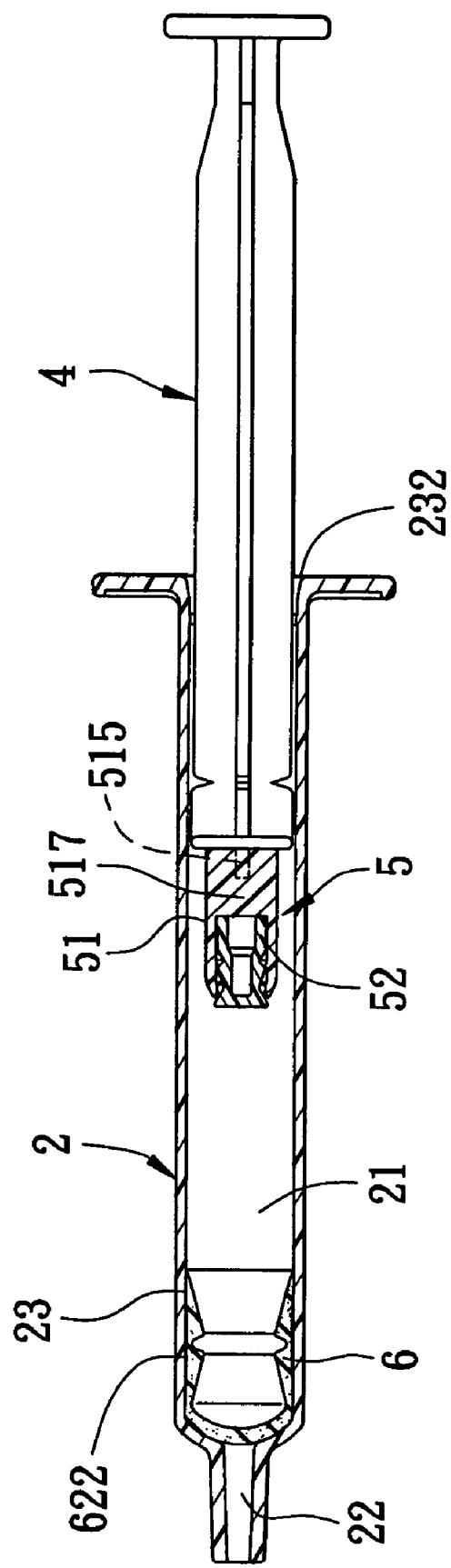

The deformable sealing member 6 includes a head end wall 613 which has a periphery and which confronts the surrounding shoulder 24, an upper sealing end 615 which is integrally formed with the periphery of the head end wall 613 and which is in fluid-tight and slidable engagement with the rear larger-diameter portion, and a deformable surrounding wall 612 which extends from the upper sealing end 615 rearwardly and which terminates at a surrounding trailing end 616 that is configured to drag on and to be in fluid-tight engagement with the rear larger-diameter portion. The deformable surrounding wall 612 has an outer surrounding wall surface 622 which is spaced apart from the rear larger-diameter portion in radial directions when the syringe is in the position of use so as to cooperative with the upper sealing end 615 and the surrounding trailing end 616 to define an annular compressible chamber 621 thereamong, thereby vesting the deformable surrounding wall 612 with an increased radial flexibility. The deformable surrounding wall 612 further has an inner surrounding wall surface 617 opposite to the outer surrounding wall surface 622 in radial directions. The inner surrounding wall surface 617 has a yielding segment 610 which is engaged with and which is depressed by the pushing region 516 radially when the carrier 5 is moved in a longitudinal direction relative to the deformable surrounding wall 612 so as to bring the head end wall 613 to abut against and to be retained at the surrounding shoulder 24, thereby displacing the syringe from the position of use to a disposal position, and a retaining segment 618 which is in a first frictional engagement with the retained region 527 by virtue of a first frictional force so as to confine, in cooperation with the yielding segment 610 and the pushing region 516, a fluid-tight surrounding area 9. Thus, referring to FIGS. 5 to 7, subsequent to the abutment of the head end wall 613 against the surrounding shoulder 24, the yielding segment 610 is depressed by the pushing region 516 radially and outwardly to result in deformation of the deformable surrounding wall 612, which moves the inner surrounding wall surface 617 radially and towards the rear larger-diameter portion so as to diminish the first frictional force, thereby disrupting the fluid-tightness of the surrounding area 9 and rendering the syringe unreusable. Subsequent to the disruption of the fluid-tightness of the surrounding area 9, the head portion 523 is blocked by the surrounding shoulder 24 from moving further so as to permit movement of the pushing segment 51 relative to the retained segment 52 such that the outer surrounding retained wall 521 is brought into a second frictional engagement with the inner surrounding engaging region 514. Meanwhile, the deformable surrounding wall 612 is deformed to squeeze the air out of the annular compressible chamber 621 so that the outer surrounding wall surface 622 is tightly attached to the rear larger-diameter portion. Subsequently, referring to FIG. 8, when the carrier 5 is moved rearwards by the plunger 4 towards the rearward opening 232, the carrier 5 is disengaged from the deformable sealing member 6.

Figure 9:
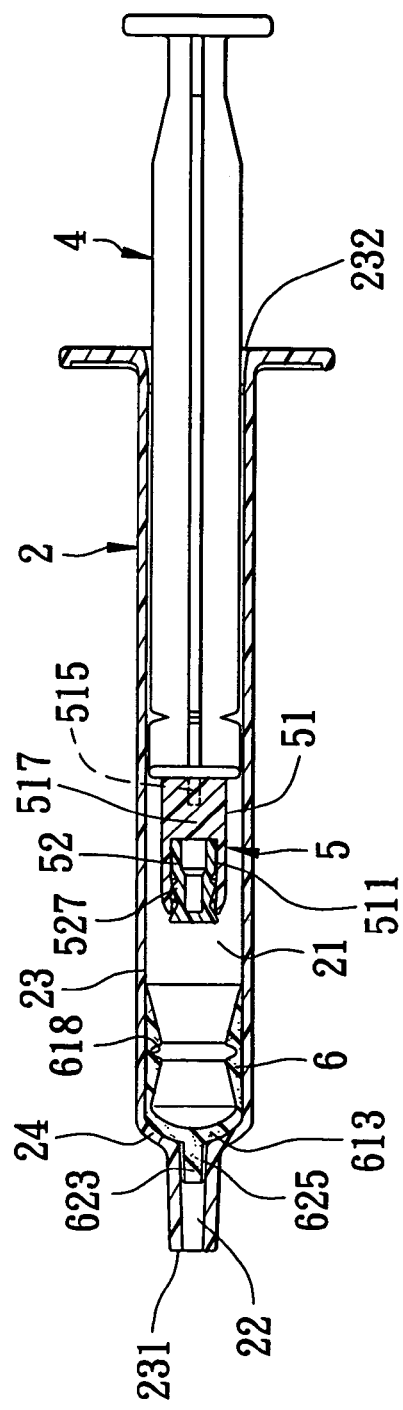
FIG. 9 is a sectional view of the second preferred embodiment of a single-use syringe according to this invention.
Figure 10:
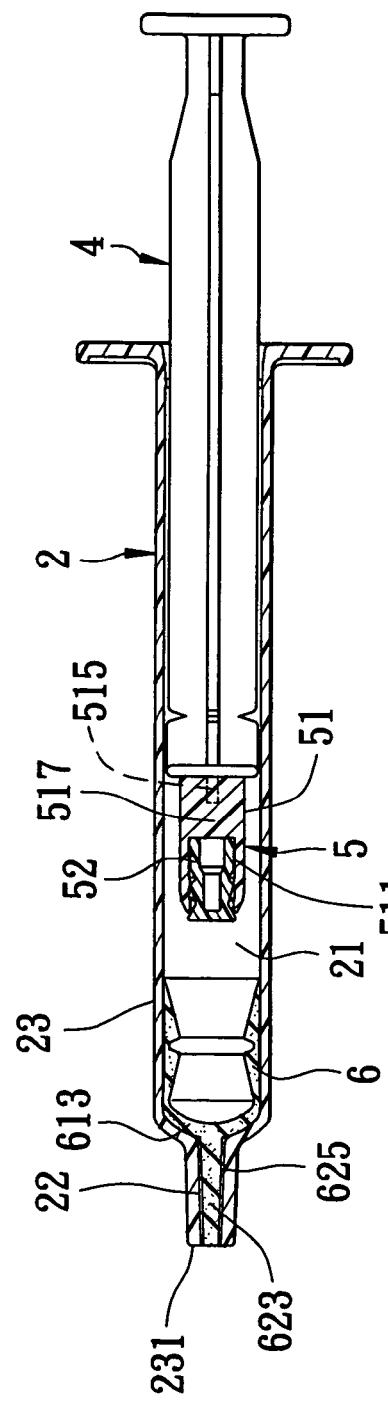
FIG. 10 is a sectional view of a modified form of the second preferred embodiment shown in FIG. 9.

Referring to FIG. 9, the second preferred embodiment of a single-use syringe according to this invention is shown to be similar to the previous embodiment in construction. The syringe of this embodiment further includes a passageway interrupting member 623 which is integrally formed with the head end wall 613 of the deformable sealing member 6 such that once the fluid-tightness of the surrounding area is disrupted, the passageway interrupting member 623 is forced by the head end wall 613 to extend into the front passageway 22. The passageway interrupting member 623 has a plurality of frictional ribs 625 disposed thereon, and a diameter larger than that of the front passageway 22 so as to be in a frictional engagement with the front smaller-diameter portion. Thus, the diminution of the first frictional force enables disengagement of the retained region 527 from the retaining segment 618, thereby facilitating disengagement of the deformable sealing member 6 from the carrier 5 when the carrier 5 is moved rearwardly by the plunger 4 toward the rearward opening 232. Alternatively, referring to FIG. 10, the passageway interrupting member 623 has a longer length so as to plug the entire front passageway 22 for minimizing the amount of medication remaining in the barrel 2.

Referring to FIGS. 11 to 13, the third preferred embodiment of a single-use syringe according to this invention is shown to be similar to the first preferred embodiment in construction. The carrier 5 of this embodiment further includes a projection member 53 which is integrally formed with the head portion 523 and which extends forwardly through a slit 619 in the head end wall 613 of the deformable sealing member 6. The projection member 53 has a diameter slightly smaller than that of the front passageway 22, and is moved with the head portion 523 by the plunger 4 to be inserted into the front passageway 22 in an injection stroke for reducing the amount of medication left in the barrel 2. When the carrier 5 is moved rearwardly, the projection member 53 is moved to disengage from the head end wall 613 of the deformable sealing member 6 so as to completely disrupt the fluid-tightness of the surrounding area. In a modified form of the embodiment, as shown in FIG. 14, the projection member 53 has a longer length so as to plug the entire front passageway 22 for minimizing the amount of medication remaining in the barrel 2.

Figure 15:
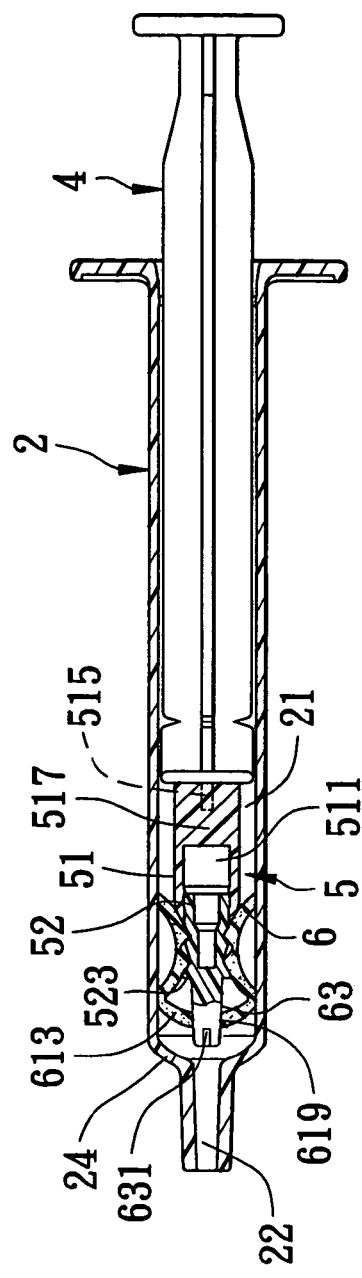
FIG. 15 is a sectional view of the fourth preferred embodiment of a single-use syringe according to this invention.
Figure 16:
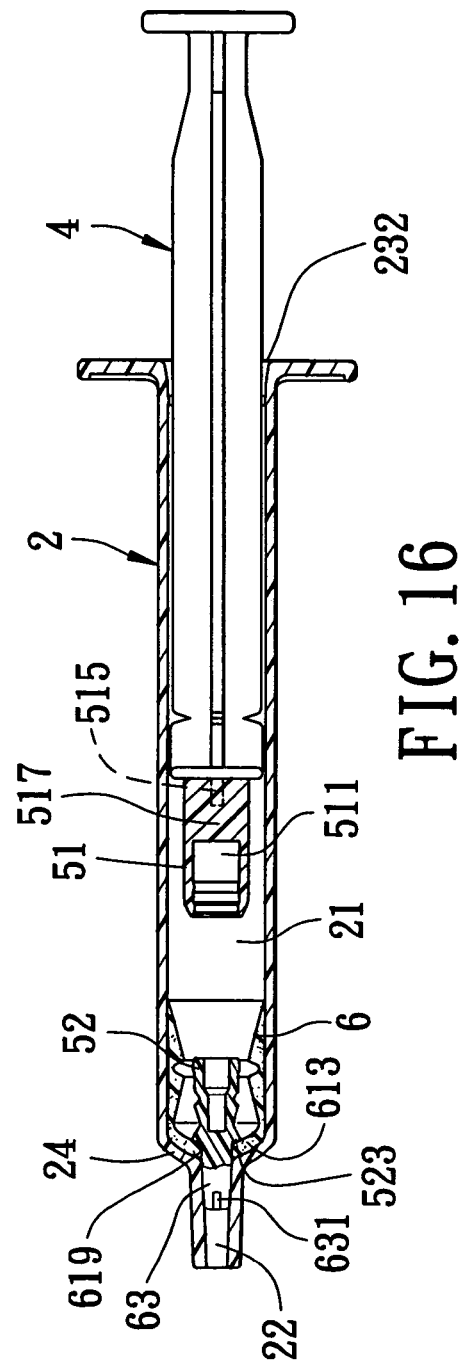
FIG. 16 is a sectional view of the fourth preferred embodiment after disruption of fluid-tightness of the syringe.

Referring to FIGS. 15 and 16, the fourth preferred embodiment of a single-use syringe according to this invention is shown to be similar to the first preferred embodiment in construction. The syringe of this embodiment further includes a passageway interrupting member 63 which is integrally formed with the head portion 523 of the carrier 5 and which projects outwardly of the head end wall 613 of the deformable sealing member 6 through a slit 619 in the head end wall 613. The passageway interrupting member 63 has a plurality of frictional ribs 631 formed thereon, and a diameter larger than that of the front passageway 22 so as to be in frictional engagement with the front smaller-diameter portion and so as to enable the head portion 523 to abut against the head end wall 613. When the tail portion 517 of the carrier 5 is moved rearwardly by the plunger 4 toward the rearward opening 232, the pushing segment 51 is disengaged from the retained segment 52 to completely disrupt the fluid-tightness of the surrounding area for rendering the syringe unreusable.

Referring to FIG. 17, a modified form of the syringe of the fourth preferred embodiment is shown to comprise a passageway interrupting member 64 which has a length sufficient to fully plug the front passageway 22. The passageway interrupting member 64 has a rear end segment 642 formed with a plurality of frictional ribs 641, and a front end segment 643 with a diameter smaller than that of the front passageway 22. Referring to FIG. 18, another modified form of the syringe of the fourth preferred embodiment is shown to comprise a passageway interrupting member 65 which has two prongs 651 that project outwardly of the forward opening 231 to acquire a biasing force so as to reinforce plugging-in engagement of the passageway interrupting member 65 with the front smaller-diameter portion.

Figure 19:
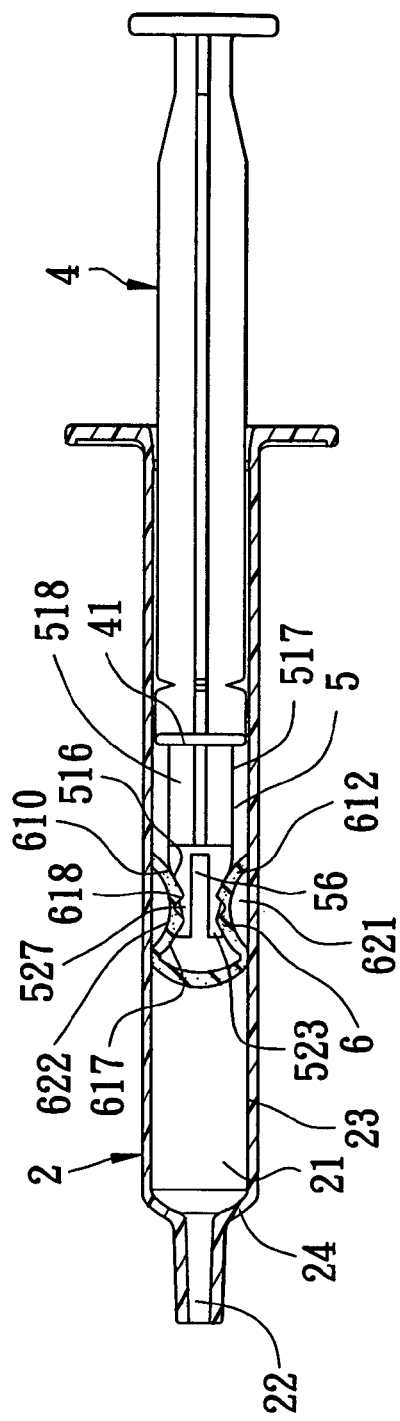
FIG. 19 is a sectional view of the fifth preferred embodiment of a single-use syringe according to this invention.
Figure 20:
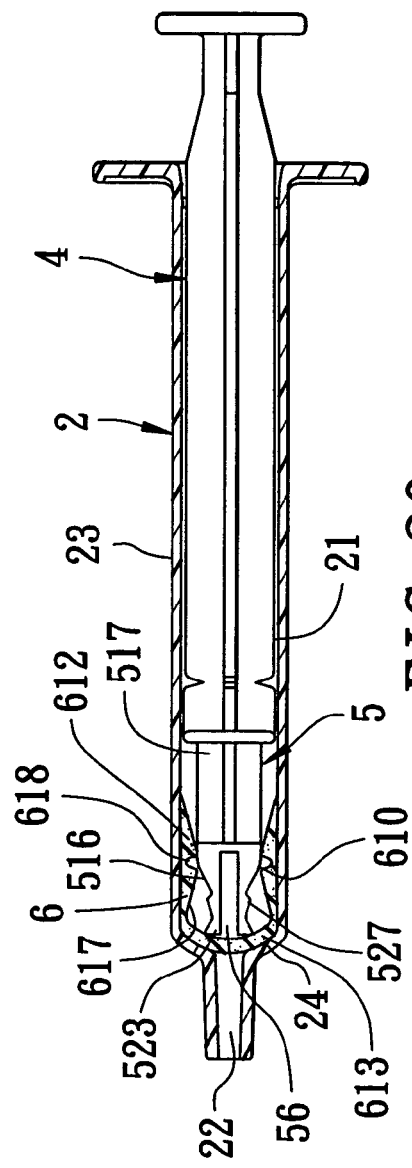

Referring to FIGS. 19 to 21, the fifth preferred embodiment of a single-use syringe according to this invention is shown to be similar to the first preferred embodiment in construction. In this embodiment, the carrier 5 and the plunger 4 are an integrally formed structure. The carrier 5 includes a tail portion 517 with a plurality of rib plates 518, and an intermediate surrounding portion extending forwardly from the tail portion 517 to terminate at a head portion 523. The intermediate surrounding portion has a pushing region 516 to depress the yielding segment 610 of the deformable sealing member 6, and a retained region 527 in frictional engagement with the retaining segment 618 of the deformable sealing member 6. The carrier 5 has an insert bore 56 extending from the head portion 523 along the axis (X) to acquire a radial flexibility so as to facilitate movement of the carrier 5 relative to the deformable sealing member 6 after abutment of the head end wall 613 against the surrounding shoulder 24.

Figure 23:
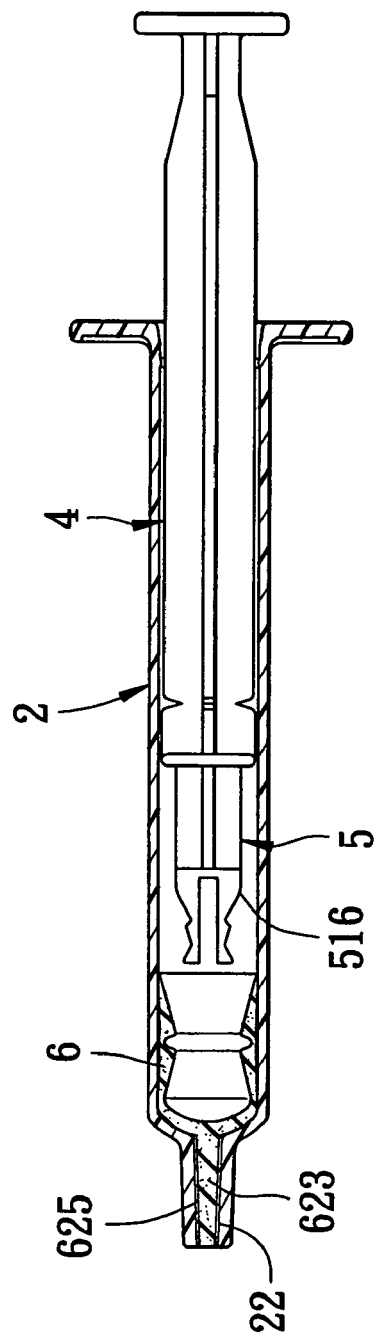
FIG. 23 is a sectional view of a modified form of the sixth preferred embodiment shown in FIG. 22.

Referring to FIGS. 22 and 23, the sixth preferred embodiment of a single-use syringe according to this invention is shown to be similar to the fifth preferred embodiment in construction. The syringe of this embodiment further includes a passageway interrupting member 623 which is integrally formed with the head end wall 613 of the deformable sealing member 6, and which has a plurality of frictional ribs 625 disposed thereon and having a diameter larger than that of the front passageway 22 so as to be in a frictional engagement with the front smaller-diameter portion, thereby facilitating disengagement of the deformable sealing member 6 from the carrier 5 when the carrier 5 is moved rearwardly by the plunger 4. Alternatively, referring to FIG. 23, the passageway interrupting member 623 may have a longer length so as to plug the entire front passageway 22 for minimizing the amount of medication remaining in the barrel 2.

Figure 24:
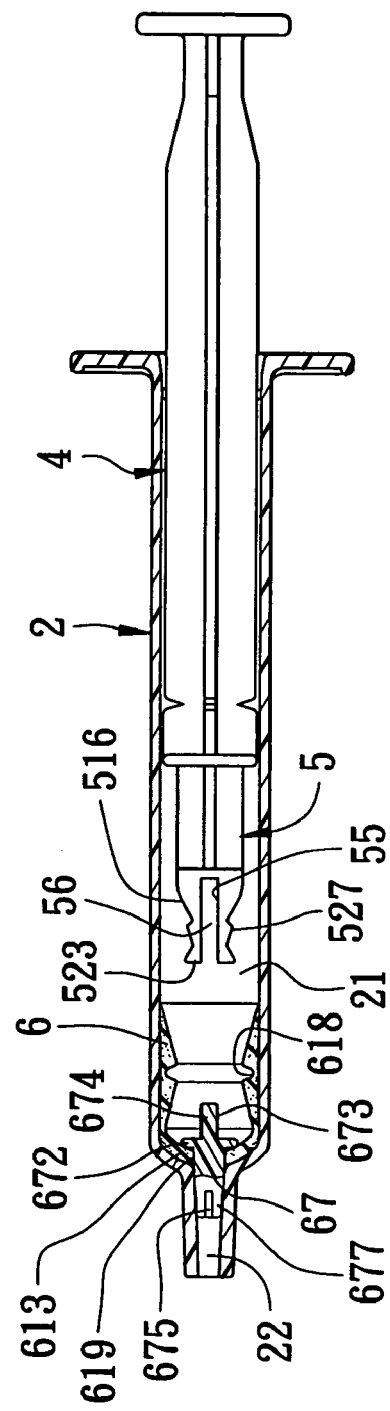
FIG. 24 is a sectional view of the seventh preferred embodiment of a single-use syringe according to this invention.
Figure 25:
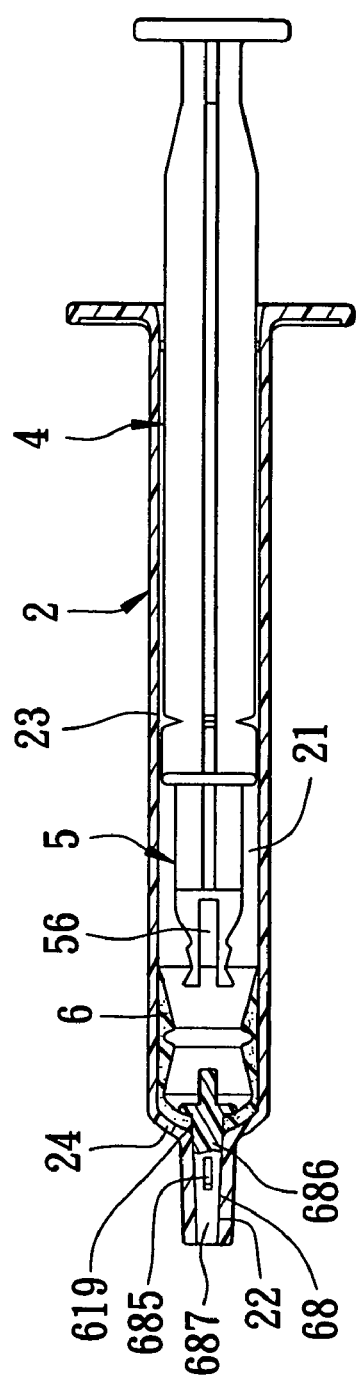
FIG. 25 is a sectional view of a modified form of the seventh preferred embodiment shown in FIG. 24.
Figure 26:
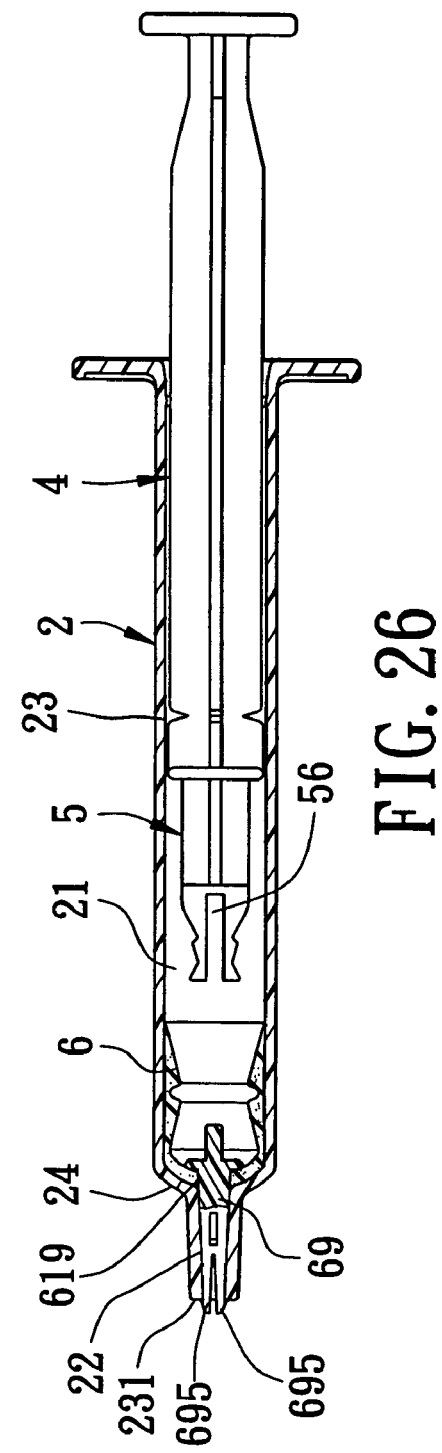
FIG. 26 is a sectional view of another modified form of the seventh preferred embodiment shown in FIG. 24.

Referring to FIGS. 24 to 26, the seventh preferred embodiment of a single-use syringe according to this invention is shown to be similar to the fifth preferred embodiment in construction. In this embodiment, the head portion 523 of the carrier 5 has an inner peripheral grip wall 55 which defines an insert bore 56 extending along the axis (X) through the intermediate surrounding portion such that the inner peripheral grip wall 55 acquires a radial flexibility, thereby yielding radially and towards the axis (X) to the first frictional force of the first frictional engagement between the retaining segment 618 and the retained region 527. The syringe further comprises a passageway interrupting member 67. The passageway interrupting member 67 has a gripped end 674 which is retained in the insert bore 56 when the inner peripheral grip wall 55 yields to the first frictional force and which has a plurality of frictional ribs 673 formed thereon, a plug head 677 which is opposite to the gripped end 674 in the longitudinal direction and which extends forwardly and outwardly of the head end wall 613 through a slit 619, and an abutment ring 672 which is disposed between the gripped end 674 and the plug head 677. The plug head 677 has a plurality of frictional ribs 675 formed thereon. Therefore, once the fluid-tightness of the surrounding area is disrupted, the plug head 677 plugs the front passageway 22 with the abutment ring 672 abutting against the head end wall 613. Referring to FIG. 25, in a modified form of the seventh preferred embodiment, the passageway interrupting member 68 has a length sufficient to fully plug the front passageway 22 for minimizing the amount of medication remaining in the barrel 2. The plug head 686 of the passageway interrupting member 68 has a rear segment formed with a plurality of frictional ribs 685, and a front end segment 687 with a diameter smaller than that of the front passageway 22. Alternatively, in another modified form of the syringe of the seventh preferred embodiment shown in FIG. 26, the passageway interrupting member 69 has two prongs 695 that project outwardly of the forward opening 231 to acquire a biasing force to reinforce plugging-in engagement of the passageway interrupting member 69 with the front smaller-diameter portion.

Figure 27:
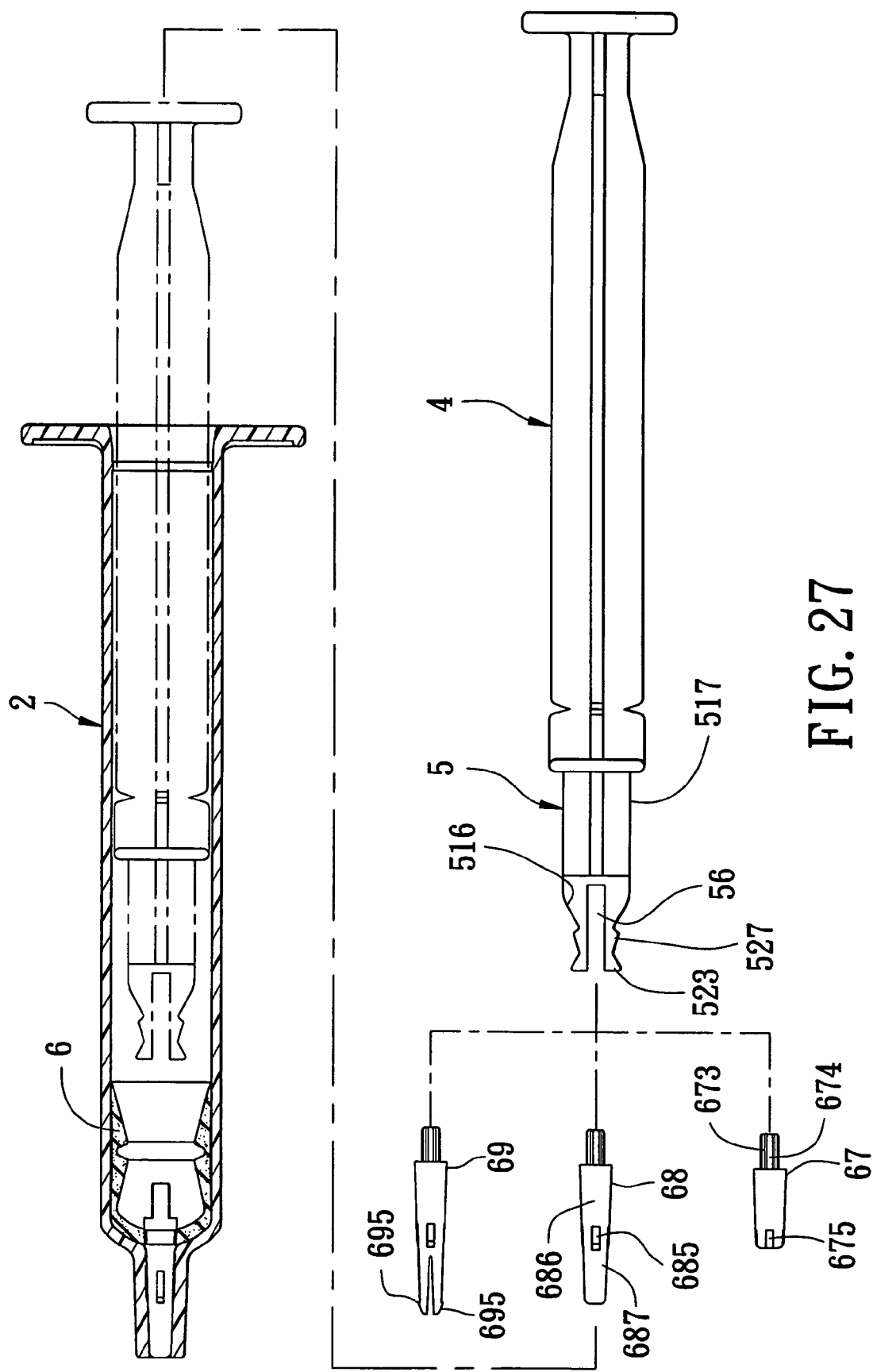
FIG. 27 is an exploded sectional view of the eighth preferred embodiment of a single-use syringe according to this invention.

Referring to FIG. 27, the eighth preferred embodiment of a single-use syringe according to this invention is shown to be similar to the seventh preferred embodiment in construction. In this embodiment, each of the passageway interrupting members 67,68,69 that are selectively insertable into the insert bore 56 is not formed with an abutment ring so as to simplify the structure thereof.

Figure 28:
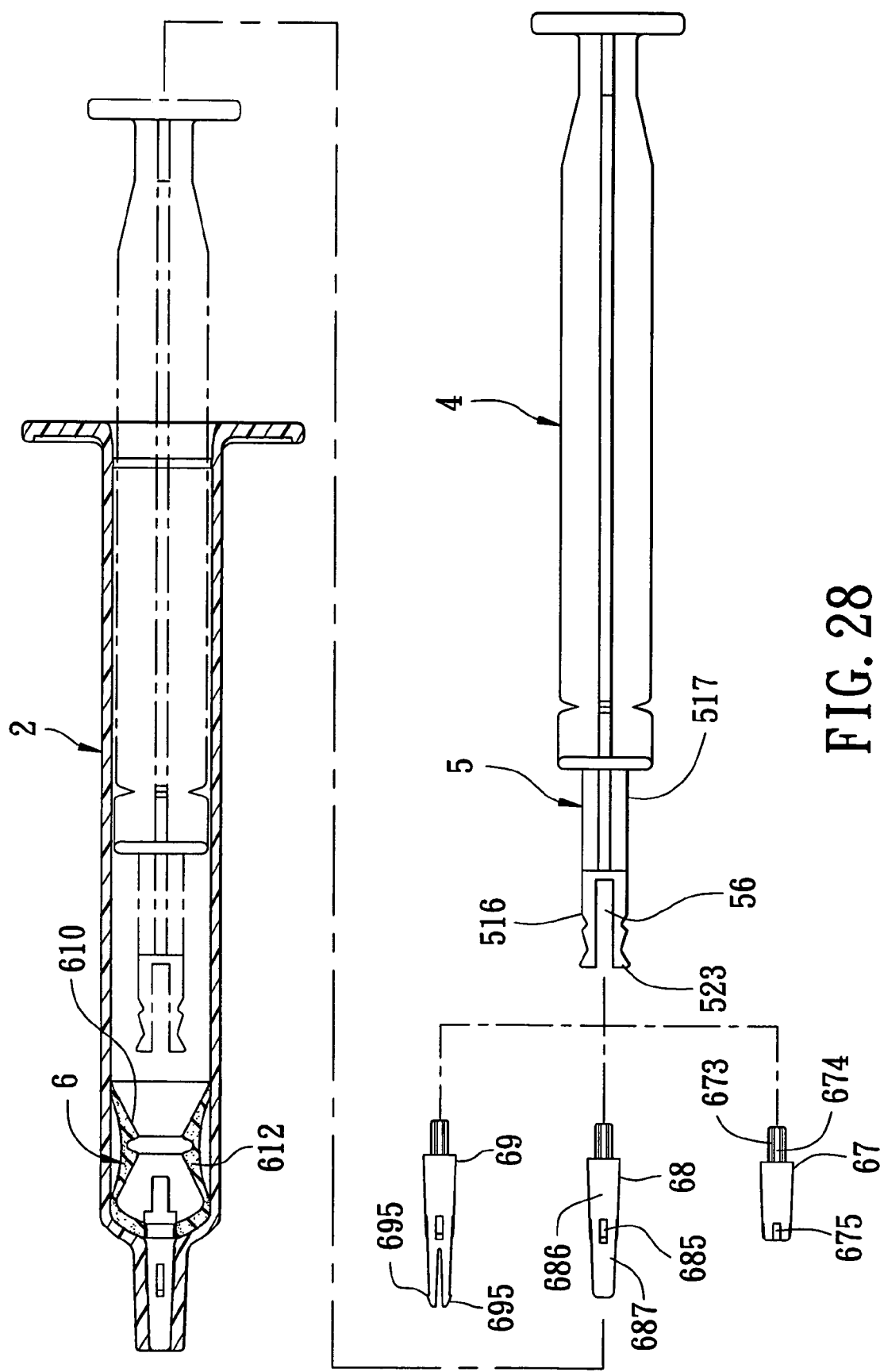
FIG. 28 is an exploded sectional view of the ninth preferred embodiment of a single-use syringe according to this invention.

Referring to FIG. 28, the ninth preferred embodiment of a single-use syringe according to this invention is shown to be similar to the eighth preferred embodiment in construction. As shown, the pushing region 516 of the carrier 5 has a relatively smooth surface. Although the yielding segment 610 of the deformable sealing member 6 is depressed by the pushing region 516 so that the deformable surrounding wall 612 is partly attached to the rear larger-diameter portion of the barrel 2, the deformable sealing member 6 may be retained by the passageway interrupting member 67,68,69 after the carrier 5 is moved rearwardly.

Figure 29:
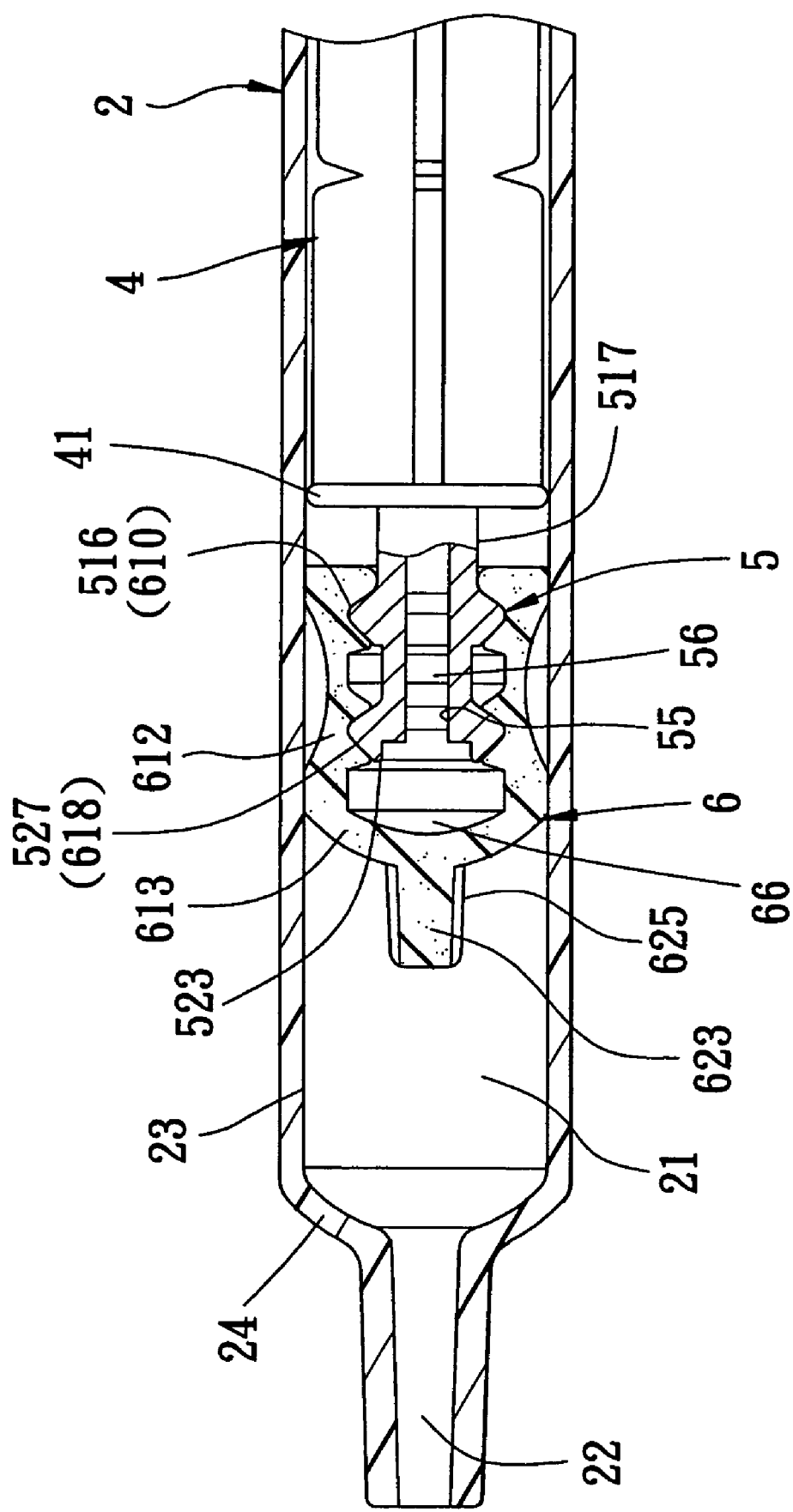
FIG. 29 is a fragmentary sectional view of the tenth preferred embodiment of a single-use syringe according to this invention.

Referring to FIGS. 29 and 30, the tenth preferred embodiment of a single-use syringe according to this invention is shown to be similar to the sixth preferred embodiment in construction. In this embodiment, the carrier 5 has two annular teeth formed on the intermediate surrounding portion to respectively serve as the pushing region 516 and the retained region 527. The deformable surrounding wall 612 has two annular grooves formed in the inner surrounding wall surface to respectively serve as the yielding segment 610 and the retaining segment 618, and a moving space 66 formed forwardly of the annular grooves. Therefore, subsequent to the abutment of the head end wall 613 against the surrounding shoulder 24, the carrier 5 can be forced to move forwardly relative to the deformable sealing member 6 to insert into the moving space 66 so as to diminish the first frictional force upon the first frictional engagement of the retained region 527 with the retaining segment 618, thereby disrupting the fluid-tightness of the surrounding area for rendering the syringe unreusable. Alternatively, the passageway interrupting member 623 may have a length sufficient to plug the entire front passageway 22 f or minimizing the amount of medication remaining in the barrel 2, as shown in FIG. 31.

Figure 32:
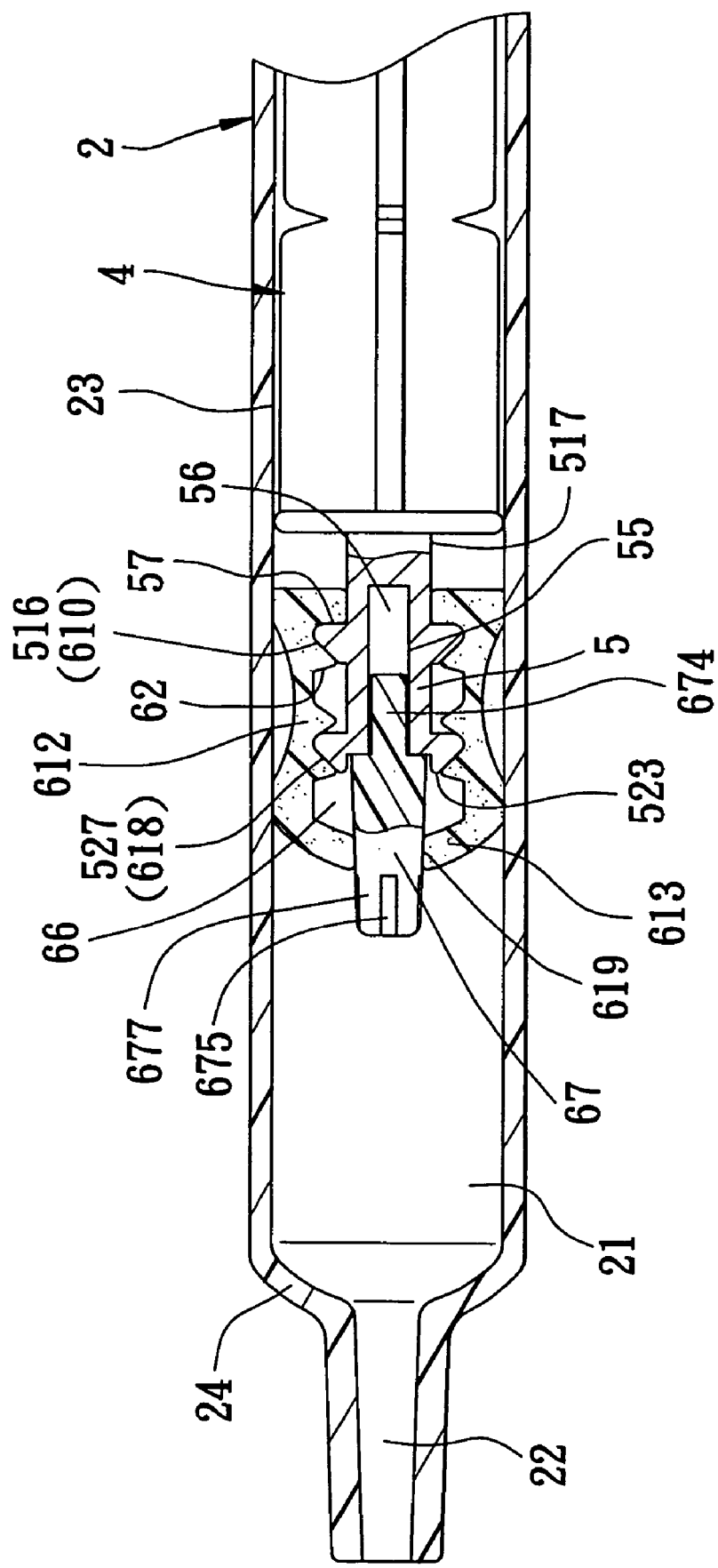
FIG. 32 is a fragmentary sectional view of the eleventh preferred embodiment of a single-use syringe according to this invention.

Referring to FIGS. 32 and 33, the eleventh preferred embodiment of a single-use syringe according to this invention is shown to be similar to the tenth preferred embodiment in construction. In this embodiment, the passageway interrupting member 67 has a gripped end 674 which is retained in the insert bore 56 when the inner peripheral grip wall 55 yields to the first frictional force of the first frictional engagement between the retaining segment 618 and the retained region 527 and which has a plurality of frictional ribs 673 formed thereon, and a plug head 677 which extends forwardly and outwardly of the head end wall 613 through a slit 619 in the head end wall 613, and which has a plurality of frictional ribs 675 formed thereon. The diminution of the first frictional force upon the first frictional engagement of the retained region 527 with the retaining segment 618 lessens the degree of yielding towards the axis (X) so as to permit the inner peripheral grip wall 55 to release the gripped end 674, thereby permitting the plug head 677 to be retained in the front passageway 22 when the carrier 5 is moved in the longitudinal direction relative to the deformable surrounding wall 612.

Furthermore, the intermediate surrounding portion of the carrier 5 further has a pulling region 57 which is disposed rearwardly of the pushing region 516. The inner surrounding wall surface of the deformable surrounding wall 612 has a pulled segment 62 which is disposed between the yielding segment 610 and the retaining segment 618. Therefore, subsequent to the movement of the carrier 5 into the moving space 66 to disrupt the fluid-tightness of the surrounding area, the pulling region 57 is displaced to abut against the pulled segment 62 such that the pulling region 57 is forced by a rearward movement of the carrier 5 to depress the pulled segment 62 to move towards the rearward opening 232, thereby permitting movement of the deformable sealing member 6 with the carrier 5 so as to bring the plug head 677 to disengage from the head end wall 613 of the deformable sealing member 6 when the plug head 677 is retained in the front passageway 22.

Figure 35:
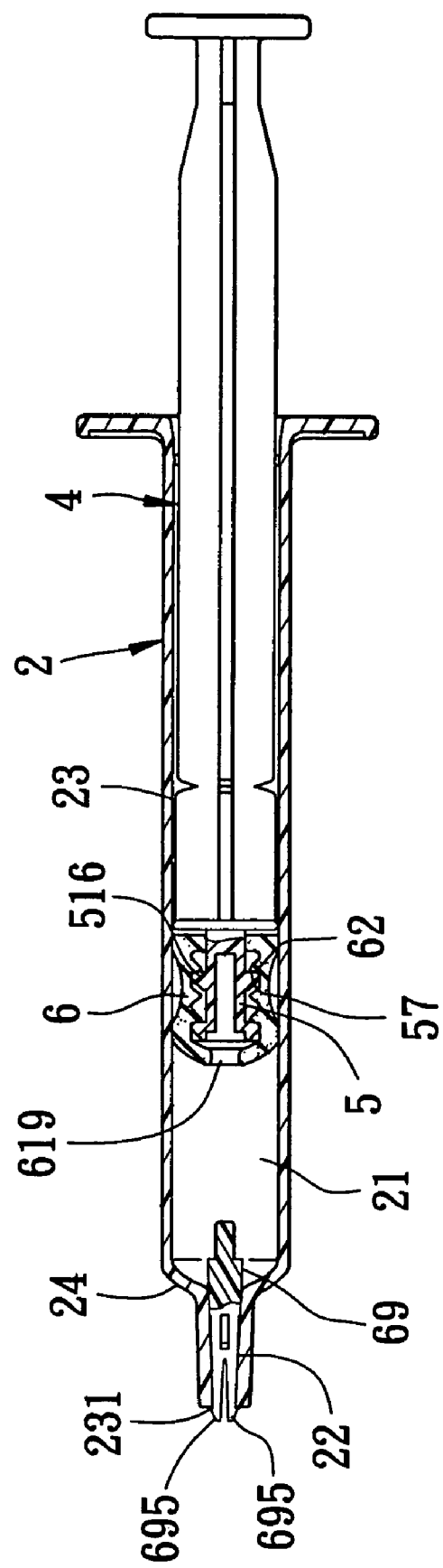
FIG. 35 is a sectional view of another modified form of the eleventh preferred embodiment shown in FIG. 32.

In the modified form of the eleventh preferred embodiment as shown in FIG. 34, the passageway interrupting member 68 has a length sufficient to plug the entire front passageway 22 for minimizing the amount of medication remaining in the barrel 2. The plug head 686 of the passageway interrupting member 68 has a rear segment formed with a plurality of frictional ribs 685, and a front end segment 687 with a diameter smaller than that of the front passageway 22. Referring to FIG. 35, in another modified form of the syringe of the eleventh preferred embodiment, the passageway interrupting member 69 has two prongs 695 that project outwardly of the forward opening 231 to acquire a biasing force to reinforce plugging-in engagement of the passageway interrupting member 69 with the front smaller-diameter portion.

Figure 36:
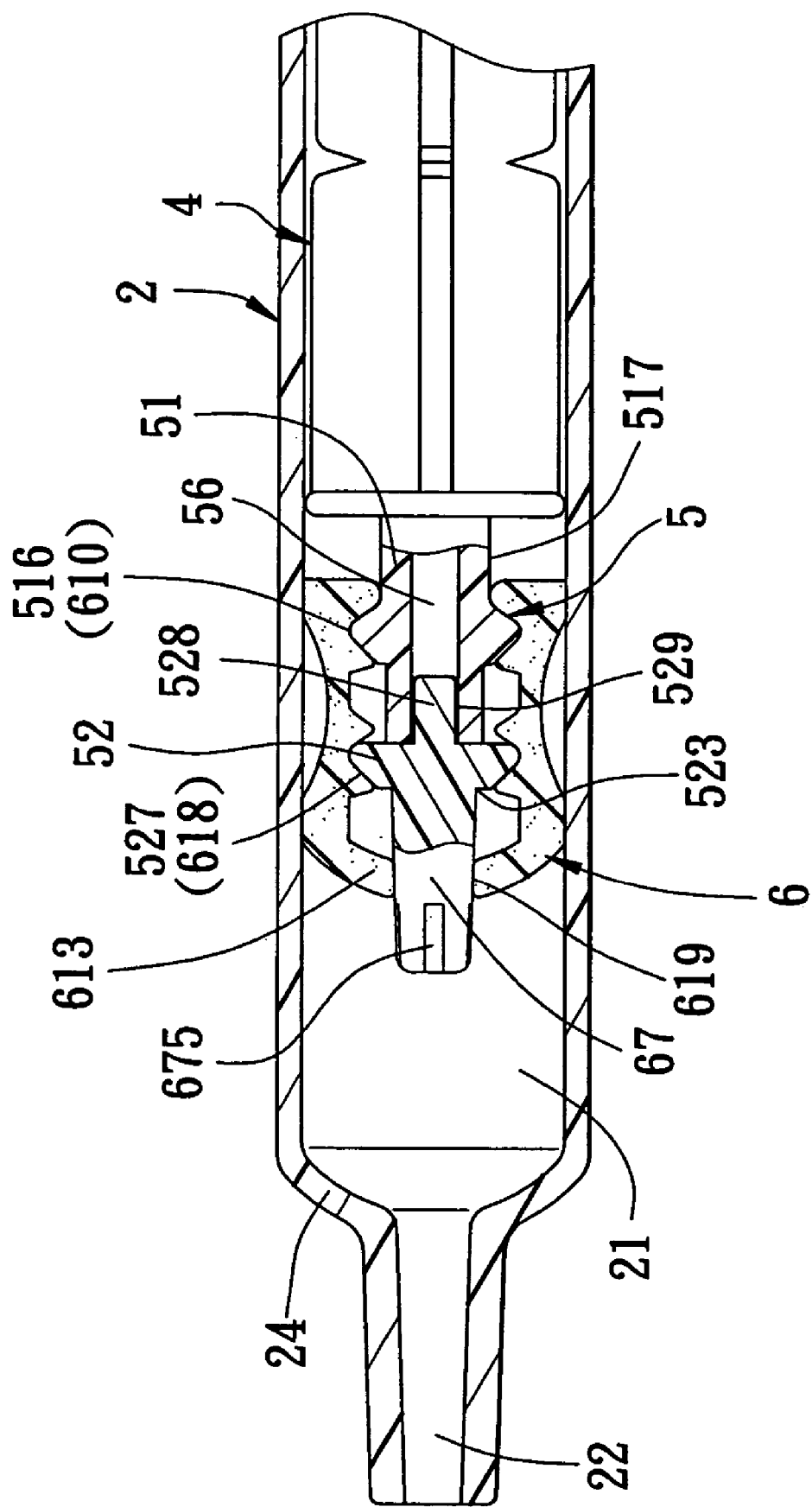
FIG. 36 is a fragmentary sectional view of the twelfth preferred embodiment of a single-use syringe according to this invention.
Figure 37:
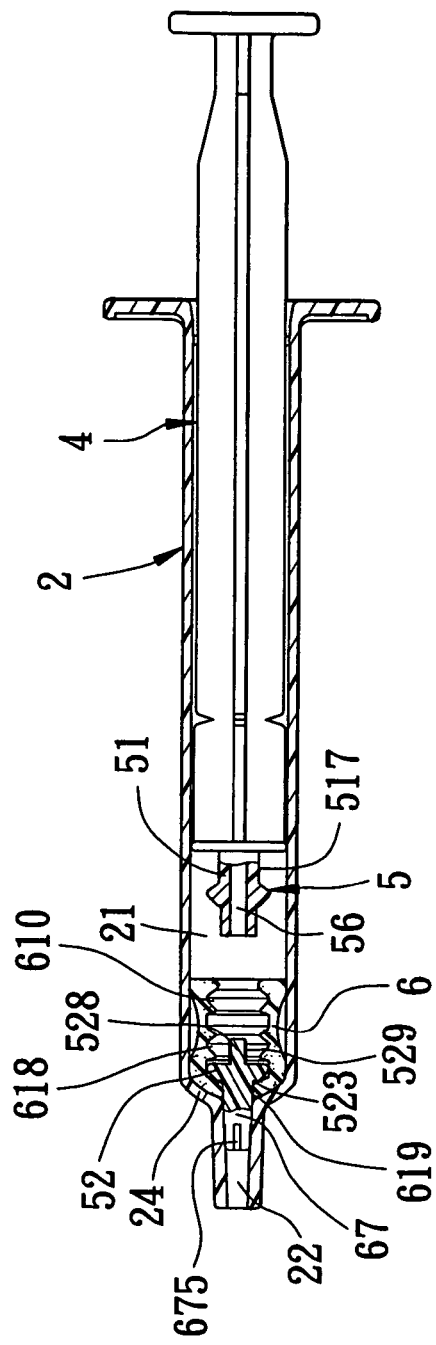
FIG. 37 is a sectional view of the twelfth preferred embodiment after disruption of the fluid-tightness of the syringe.

Referring to FIGS. 36 and 37, the twelfth preferred embodiment of a single-use syringe according to this invention is shown to be similar to the eleventh preferred embodiment in construction. In this embodiment, the intermediate surrounding portion of the carrier 5 includes a tubular pushing segment 51 with the pushing region 516, and a tubular retained segment 52 with the retained region 527. The pushing segment 51 has an insert bore 56 extending along the axis (X). The retained segment 52 has a grip portion 528 which is retained in the insert bore 56, and which has a plurality of frictional ribs 529 formed thereon. The passageway interrupting member 67 is integrally formed with the head portion 523, extends forwardly and outwardly of the head end wall 613 through the slit 619, and has a plurality of frictional ribs 675 formed thereon. Therefore, subsequent to the disruption of the fluid-tightness of the surrounding area, the head portion 523 is brought to abut against the head end wall 613 so as to permit the passageway interrupting member 67 to plug the front passageway 22.

Figure 38:
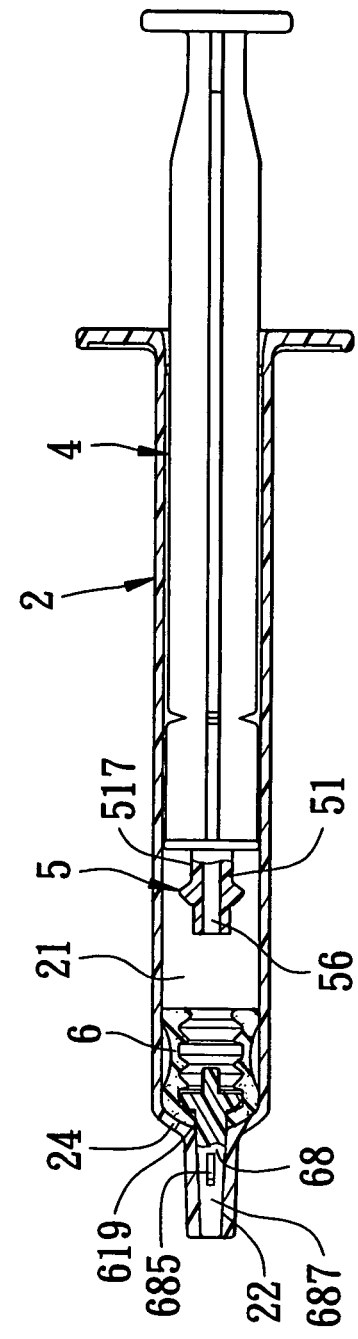
FIG. 38 is a sectional view of a modified form of the twelfth preferred embodiment shown in FIG. 36.
Figure 39:
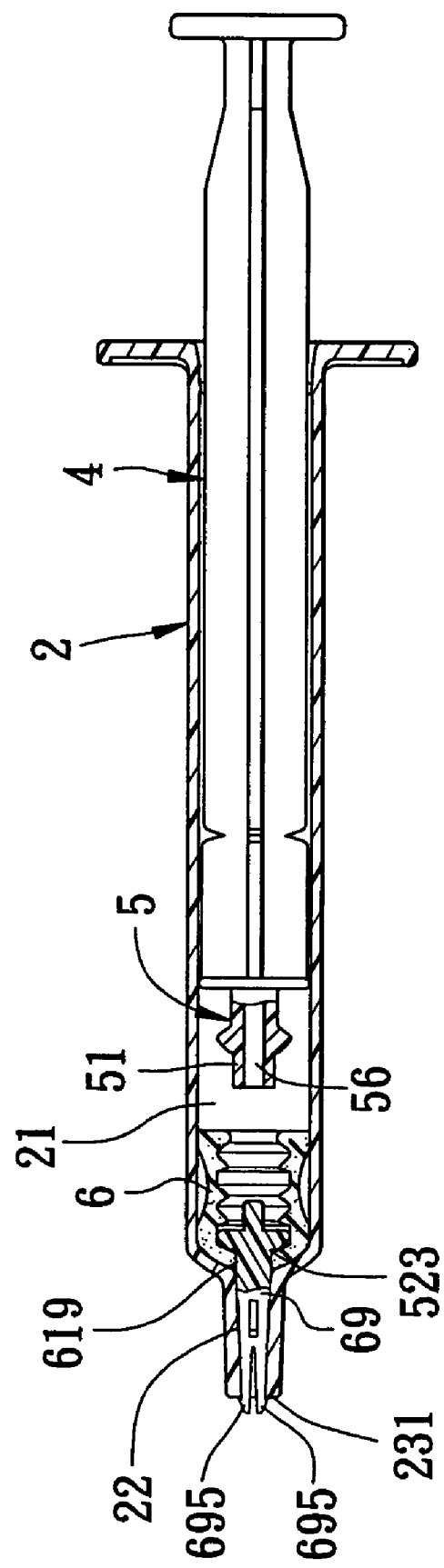
FIG. 39 is a sectional view of another modified form of the twelfth preferred embodiment shown in FIG. 36.

In the modified form of the twelfth preferred embodiment as shown in FIG. 38, the passageway interrupting member 68 has a length sufficient to plug the entire front passageway 22 for minimizing the amount of medication remaining in the barrel 2. The passageway interrupting member 68 has a rear segment formed with a plurality of frictional ribs 685, and a front end segment 687 with a diameter smaller than that of the front passageway 22. Referring to FIG. 39, in another modified form of the syringe of the twelfth preferred embodiment, the passageway interrupting member 69 has two prongs 695 that project outwardly of the forward opening 231 to acquire a biasing force to reinforce plugging-in engagement of the passageway interrupting member 69 with the front smaller-diameter portion.

As illustrated, in the syringe of this invention, during displacement of the syringe from the position of use to the disposal position, the first frictional force, by which the retaining segment 618 of the deformable sealing member 6 is in frictional engagement with the retained region 527 of the carrier 5, is diminished when the yielding segment 610 is depressed by the pushing region 516, thereby facilitating release of the retained region 527 from the retaining segment 618 to ensure disruption of the fluid-tightness of the surrounding area for rendering the syringe unreusable. Moreover, the passageway interrupting member 623,63,64,65,67, 68,69 is provided to plug the front passageway 22 of the barrel 2 even when the plunger 4 is moved rearwardly, thereby preventing the syringe from being reused. Also, the passageway interrupting member 623,63,64,65,67,68,69 can be coupled with one of the head portion 523 of the carrier 5 and the head end wall 613 of the deformable sealing member 6. Therefore, the barrel 2, the carrier 5, the plunger 4, and the passageway interrupting member can be fabricated conveniently without the need to modify the barrel 2.

While the present invention has been described in connection with what are considered the most practical and preferred embodiments, it is understood that this invention is not limited to the disclosed embodiments but is intended to cover various arrangements included within the spirit and cope of the broadest interpretations and equivalent arrangements.

We claim:

1. A single-use syringe adapted to be used with a needle assembly, comprising:

a barrel having an inner surrounding barrel surface which surrounds an axis in a longitudinal direction, and which includes a rear larger-diameter portion that defines a rear passageway therein, a front smaller-diameter portion that defines a front passageway therein to be in fluid communication with the needle assembly and that is opposite to said rear larger-diameter portion in the longitudinal direction, and a surrounding shoulder that is disposed between said rear larger-diameter portion and said front smaller-diameter portion, said rear passageway terminating at a rearward opening;

a plunger which is disposed to be movable in said rear passageway along said rear larger-diameter portion, said plunger having a front end wall which confronts said front passageway, and a rear end wall which is disposed opposite to said front end wall and which extends outwardly of said rearward opening to be manually operable;

a carrier including a tail portion which extends from said front end wall along the axis, a head portion which is disposed opposite to said tail portion in said rear passageway along the axis, and an intermediate surrounding portion which is interposed between said tail and head portions and which surrounds the axis, said intermediate surrounding portion having a pushing region and a retained region which are proximate to said tail and head portions, respectively; and a hollow deformable sealing member including a head end wall which has a periphery and which confronts said surrounding shoulder, an upper sealing end which is integrally formed with said periphery of said head end wall and which is in fluid-tight and slidable engagement with said rear larger-diameter portion, and a deformable surrounding wall which extends from said upper sealing end rearwardly and which terminates at a surrounding trailing end that is configured to drag on said rear larger-diameter portion, said deformable surrounding wall having an outer surrounding wall surface which is spaced apart from said rear larger-diameter portion in radial directions when said syringe is in a position of use, thereby vesting said deformable surrounding wall with an increased radial flexibility, and an inner surrounding wall surface which is opposite to said outer surrounding wall surface in radial directions, said inner surrounding wall surface having a yielding segment which is engaged with and which is depressed by said pushing region radially when said carrier is moved in a longitudinal direction relative to said deformable surrounding wall so as to bring said head end wall to abut against and to be retained at said surrounding shoulder, thereby displacing said syringe from the position of use to a disposal position, and a retaining segment which is in a first frictional engagement with said retained region by virtue of a first frictional force so as to confine, in cooperation with said yielding segment and said pushing region, a fluid-tight surrounding area, and which is configured such that the first frictional force is diminished so as to facilitate release of said retained region from said retaining segment when said yielding segment is depressed by said pushing region, thereby disrupting fluid-tightness of said surrounding area and rendering the syringe unreusable.

2. The single-use syringe of claim 1, wherein said surrounding trailing end of said deformable surrounding wall is in fluid-tight and slidable engagement with said rear larger-diameter portion, said outer surrounding wall surface of said deformable surrounding wall being configured to cooperate with said upper sealing end to define an annular compressible chamber between said upper sealing end and said surrounding trailing end such that, subsequent to abutment of said head end wall against said surrounding shoulder, said yielding segment is depressed by said pushing region radially and outwardly to result in deformation of said deformable surrounding wall which moves said inner surrounding wall surface radially and towards said rear larger-diameter portion so as to diminish the first frictional force, thereby disrupting the fluid-tightness of said surrounding area, and facilitating disengagement of said carrier from said deformable sealing member when said carrier is moved rearwards by said plunger towards said rearward opening.

3. The single-use ,syringe of claim 2, wherein said intermediate surrounding portion of said carrier includes
  a tubular pushing segment serving as said pushing region, said tubular pushing segment being coupled and formed integrally with said tail portion, and terminating at an opened end, said tubular pushing segment having an inner surrounding engaging region which extends in the longitudinal direction to be communicated with said opened end, and which surrounds the axis to define a cavity, and
  a tubular retained segment serving as said retained region, said tubular retained segment having an outer surrounding retained wall which extends from said head portion in the longitudinal direction to terminate at an outer engaging end and which is configured to be insertable into said cavity to bring said outer surrounding retained wall into a second frictional engagement with said inner surrounding engaging region such that, subsequent to the disruption of the fluid-tightness of said surrounding area, said head portion is blocked by said surrounding shoulder from moving further so as to permit said outer surrounding retaining wall to be in the second frictional engagement with said inner surrounding engaging region, thereby facilitating disengagement of said carrier from said deformable sealing member.

4. The single-use syringe of claim 3, wherein said tubular pushing segment has a vent hole in fluid communication with said cavity.

5. The single-use syringe of claim 2, wherein said deformable surrounding wall is configured such that when said inner surrounding wall surface is moved radially and towards said rear larger-diameter portion, said deformable surrounding wall squeezes air out of said annular compressible chamber so as to permit said outer surrounding wall surface to abut against said rear larger-diameter portion.

6. The single-use syringe of claim 1, further comprising a passageway interrupting member which is disposed to be engaged with one of said head portion of said carrier and said head end wall of said deformable sealing member, and which is configured such that once the fluid-tightness of said surrounding area is disrupted, said passageway interrupting member is forced by a corresponding one of the said head portion and said head end wall to plug said front passageway.

7. The single-use syringe of claim 6, wherein said passageway interrupting member has frictional ribs disposed thereon for frictional engagement with said front smaller-diameter portion.

8. The single-use syringe of claim 6, wherein said passageway interrupting member has two prongs which acquire a biasing force to reinforce plugging-in engagement of said passageway interrupting member with said front smaller-diameter portion.

9. The single-use syringe of claim 6, wherein said passageway interrupting member is integrally formed with the corresponding one of said head portion and said head end wall such that once the fluid-tightness of said surrounding area is disrupted, the diminution of the first frictional force enables disengagement of said retained region from said retaining segment, thereby permitting disengagement of said deformable sealing member from said carrier when said carrier is moved rearwards by said plunger toward said rearward opening.

10. The single-use syringe of claim 6, wherein said head portion of said carrier has an inner peripheral grip wall which defines an insert bore extending along the axis through said intermediate surrounding portion and which is of a dimension such that said inner peripheral grip wall acquires a radial flexibility, thereby yielding radially and towards the axis to the first frictional force so as to facilitate disruption of the fluid-tightness of said surrounding area.

11. The single-use syringe of claim 10, wherein said passageway interrupting member has a gripped end which is retained in said insert bore when said inner peripheral grip wall yields to the first frictional force, and a plug head which is opposite to said gripped end in the longitudinal direction, and which extends forwardly and outwardly of said head end wall of said deformable sealing member such that once the fluid-tightness of said surrounding area is disrupted, the diminution of the first frictional force upon the first frictional engagement lessens the degree of yielding towards the axis so as to permit said inner peripheral grip wall to release said gripped end, thereby permitting said plug head to be retained in said front passageway when said carrier is moved in the longitudinal direction relative to said deformable surrounding wall.

12. The single-use syringe of claim 11, wherein said intermediate surrounding portion has a pulling region which is disposed rearwardly of said pushing region, said inner surrounding wall surface of said deformable surrounding wall having a pulled segment which is disposed between said yielding segment and said retaining segment and which is configured such that said pulling region is displaced to abut against said pulled segment subsequent to disruption of the fluid-tightness of said surrounding area, and such that said pulling region is forced by a rearward movement of said carrier to depress said pulled segment to move towards said rearward opening, thereby permitting movement of said deformable sealing member with said carrier so as to bring said plug head to disengage from said head end wall of said deformable sealing member when said plug head is retained in said front passageway.

13. The single-use syringe of claim 1, wherein said carrier includes a projection member which is integrally formed with said head portion and which extends through said head end wall of said deformable sealing member such that when said carrier is moved rearwards, said projection member is disengaged from said head end wall of said deformable sealing member.

14. A single-use syringe adapted to be used with a needle assembly, comprising:

a barrel having an inner surrounding barrel surface which surrounds an axis in a longitudinal direction, and which includes a rear larger-diameter portion that defines a rear passageway therein, a front smaller-diameter portion that defines a front passageway therein to be in fluid communication with the needle assembly and that is opposite to said rear larger-diameter portion in the longitudinal direction, and a surrounding shoulder that is disposed between said rear larger-diameter portion and said front smaller-diameter portion, said rear passageway terminating at a rearward opening;

a plunger which is disposed to be movable in said rear passageway along said rear larger-diameter portion, said plunger having a front end wall which confronts said front passageway, and a rear end wall which is disposed opposite to said front end wall and which extends outwardly of said rearward opening to be manually operable;

a carrier including a tail portion which extends from said front end wall along the axis, a head portion which is disposed opposite to said tail portion in said rear passageway along the axis, and an intermediate surrounding portion which is interposed between said tail and head portions and which surrounds the axis, said intermediate surrounding portion having a pushing region and a retained region which are proximate to said tail and head portions, respectively; and a hollow deformable sealing member including a head end wall which has a periphery and which confronts said surrounding shoulder, an upper sealing end which is integrally formed with said periphery of said head end wall and which is in fluid-tight and slidable engagement with said rear larger-diameter portion, and a deformable surrounding wall which extends from said upper sealing end rearwardly and which terminates at a surrounding trailing end that is configured to drag on said rear larger-diameter portion, said deformable surrounding wall having an outer surrounding wall surface which is spaced apart from said rear larger-diameter portion in radial directions when said syringe is in a position of use, thereby vesting said deformable surrounding wall with an increased radial flexibility, and an inner surrounding wall surface which is opposite to said outer surrounding wall surface in radial directions, said inner surrounding wall surface having a yielding segment which is engaged with and which is moved by said pushing region in a radial direction and is thereby radially deformed when said carrier is moved in a longitudinal direction relative to said deformable surrounding wall so as to bring said head end wall to abut against and to be retained at said surrounding shoulder, thereby displacing said syringe from the position of use to a disposal position, and a retaining segment which is in a first frictional engagement with said retained region by virtue of a first frictional force so as to confine, in cooperation with said yielding segment and said pushing region, a fluid-tight surrounding area, and which is configured such that the first frictional force is diminished so as to facilitate release of said retained region from said retaining segment when said yielding segment is depressed by said pushing region, thereby disrupting fluid-tightness of said surrounding area and rendering the syringe unreusable.

* * * * *